(12) United States Patent
Matouschek

(10) Patent No.: US 11,008,372 B2
(45) Date of Patent: May 18, 2021

(54) TARGETING PROTEINS FOR DEGRADATION

(71) Applicants: BOARD OF REGENTS, THE UNIVERSITY OF TEXAS SYSTEM, Austin, TX (US); NORTHWESTERN UNIVERSITY, Evanston, IL (US)

(72) Inventor: Andreas Matouschek, Austin, TX (US)

(73) Assignees: BOARD OF REGENTS, THE UNIVERSITY OF TEXAS SYSTEM, Austin, TX (US); NORTHWESTERN UNIVERSITY, Evanston, IL (US)

( * ) Notice: Subject to any disclaimer, the term of this patent is extended or adjusted under 35 U.S.C. 154(b) by 110 days.

(21) Appl. No.: 15/773,228

(22) PCT Filed: Nov. 7, 2016

(86) PCT No.: PCT/US2016/060787
§ 371 (c)(1),
(2) Date: May 3, 2018

(87) PCT Pub. No.: WO2017/079723
PCT Pub. Date: May 11, 2017

(65) Prior Publication Data
US 2018/0327462 A1    Nov. 15, 2018

Related U.S. Application Data

(60) Provisional application No. 62/252,472, filed on Nov. 7, 2015.

(51) Int. Cl.
| | |
|---|---|
| *C07K 14/47* | (2006.01) |
| *C12N 9/64* | (2006.01) |
| *C07K 14/435* | (2006.01) |
| *A61K 38/00* | (2006.01) |
| *C07K 14/00* | (2006.01) |
| *A61P 35/00* | (2006.01) |
| *A61K 38/17* | (2006.01) |
| *C12N 15/113* | (2010.01) |

(52) U.S. Cl.
CPC .............. *C07K 14/47* (2013.01); *A61K 38/00* (2013.01); *A61K 38/1709* (2013.01); *A61P 35/00* (2018.01); *C07K 14/00* (2013.01); *C07K 14/435* (2013.01); *C12N 9/6421* (2013.01); *C12N 15/1135* (2013.01)

(58) Field of Classification Search
None
See application file for complete search history.

(56) References Cited

U.S. PATENT DOCUMENTS

| | | |
|---|---|---|
| 5,844,094 A | 12/1998 | Hudson et al. |
| 2005/0152888 A1 | 7/2005 | Church et al. |
| 2010/0129933 A1 | 5/2010 | Arts et al. |

FOREIGN PATENT DOCUMENTS

| | | | | |
|---|---|---|---|---|
| WO | WO 2014/047741 | | 4/2014 | |
| WO | WO-2014047741 A1 | * | 4/2014 | ........... A61K 38/482 |

OTHER PUBLICATIONS

Sugasawa et al (Mol. Cell. Biol., 16:4852-4861, 1996).*
Bhattacharyya, Sucharita, et al. "Regulated protein turnover: snapshots of the proteasome in action." *Nature Reviews Molecular Cell Biology* 15.2 (2014): 122-133.
Bonger, Kimberly M., et al. "Small-molecule displacement of a cryptic degron causes conditional protein degradation." *Nature Chemical Biology* 7.8 (2011): 531.
Fishbain, Susan, et al. "Sequence composition of disordered regions fine-tunes protein half-life." *Nature Structural & Molecular Biology* 22.3 (2015): 214-221.
Inobe, Tomonao, and Andreas Matouschek. "Paradigms of protein degradation by the proteasome." *Current Opinion in Structural Biology* 24 (2014): 156-164.
International Preliminary Report on Patentability issued in International Application No. PCT/US2016/060787, dated May 17, 2018.
International Search Report and Written Opinion issued in International Application No. PCT/US2016/060787, dated Jan. 24, 2017.
Schrader, Erin K., et al. "A three-part signal governs differential processing of Gli1 and Gli3 proteins by the proteasome." *Journal of Biological Chemistry* 286.45 (2011): 39051-39058.
Takahashi, Kazunobu, Andreas Matouschek, and Tomonao Inobe. "Regulation of proteasomal degradation by modulating proteasomal initiation regions." *ACS Chemical Biology* 10.11 (2015): 2537-2543.
Wilmington, Shameika R., and Andreas Matouschek. "An inducible system for rapid degradation of specific cellular proteins using proteasome adaptors." *PloS One* 11.4 (2016).

* cited by examiner

*Primary Examiner* — Brian Gangle
(74) *Attorney, Agent, or Firm* — Parker Highlander PLLC

(57) ABSTRACT

Embodiments provided here include recombinant polypeptides, termed degradons, comprising a target binding domain and a proteasome-binding domain. Degradons of the embodiments are able to selectively target and degrade proteins bound by the target-binding domain, such as proteins associated with disease. Vectors encoding degradons and methods of treating disease with degradons and degradon expression vectors are likewise provided.

21 Claims, 28 Drawing Sheets

Specification includes a Sequence Listing.

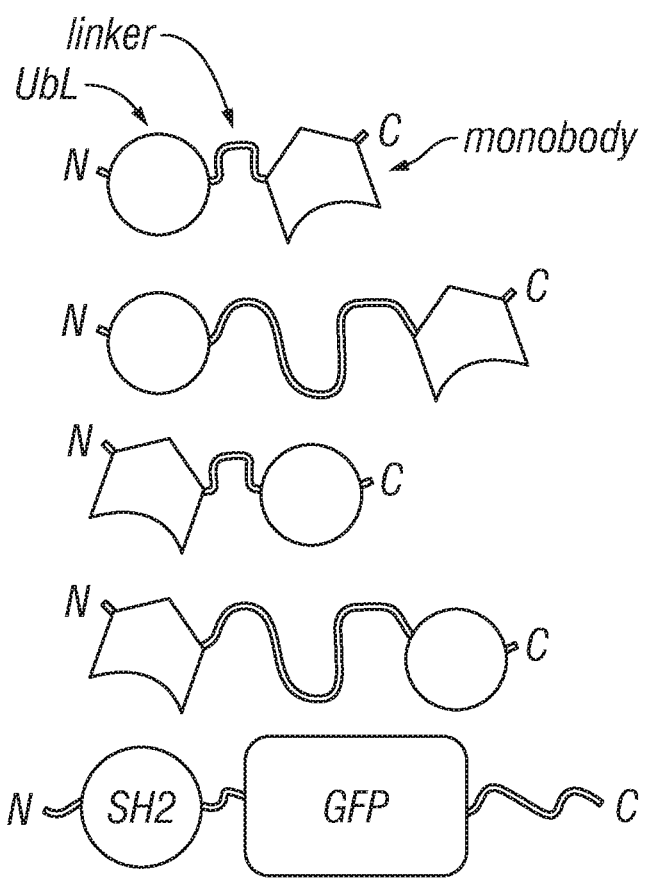
FIG. 2
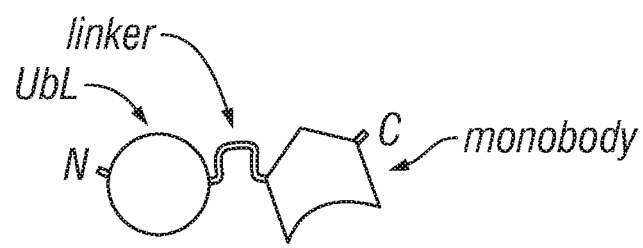
FIG. 3A

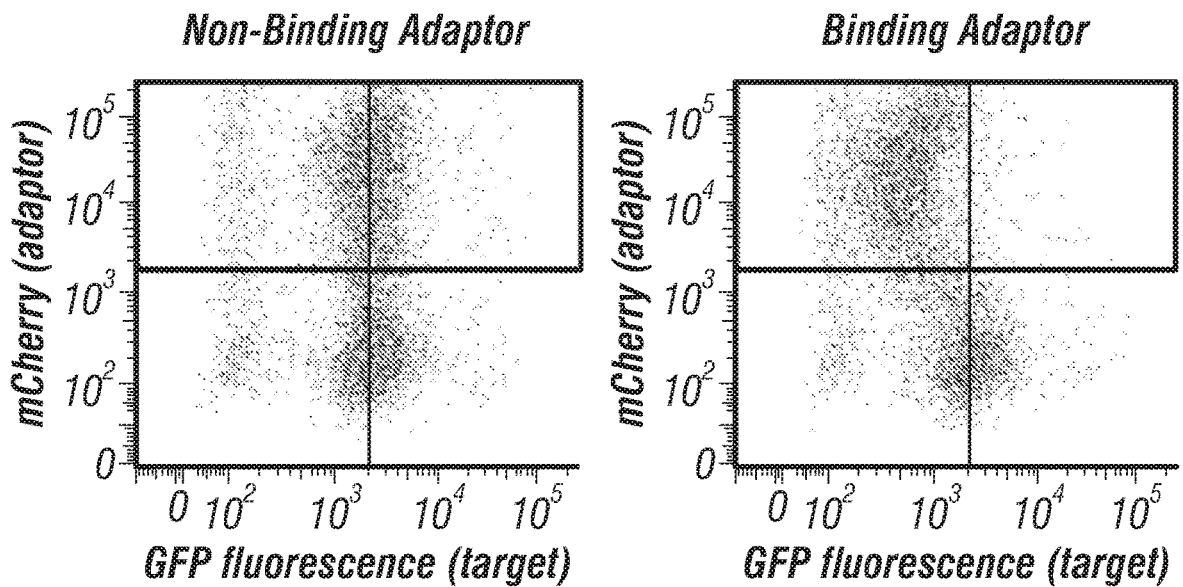
FIG. 6B
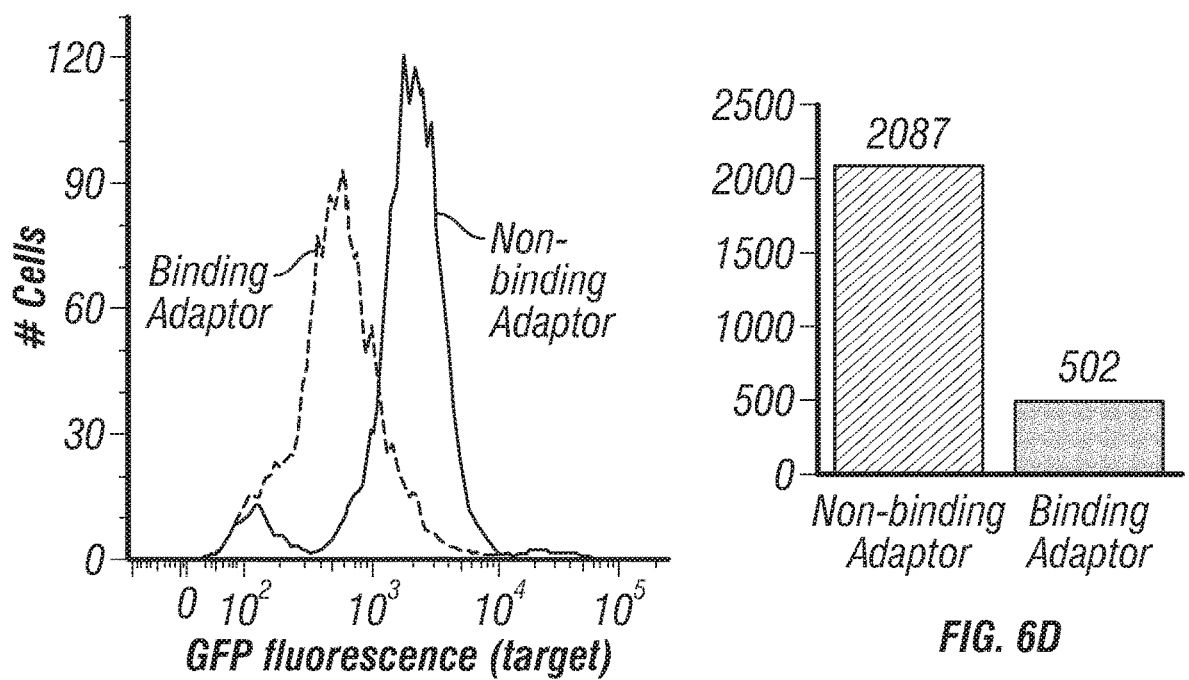
FIG. 6C
FIG. 6D

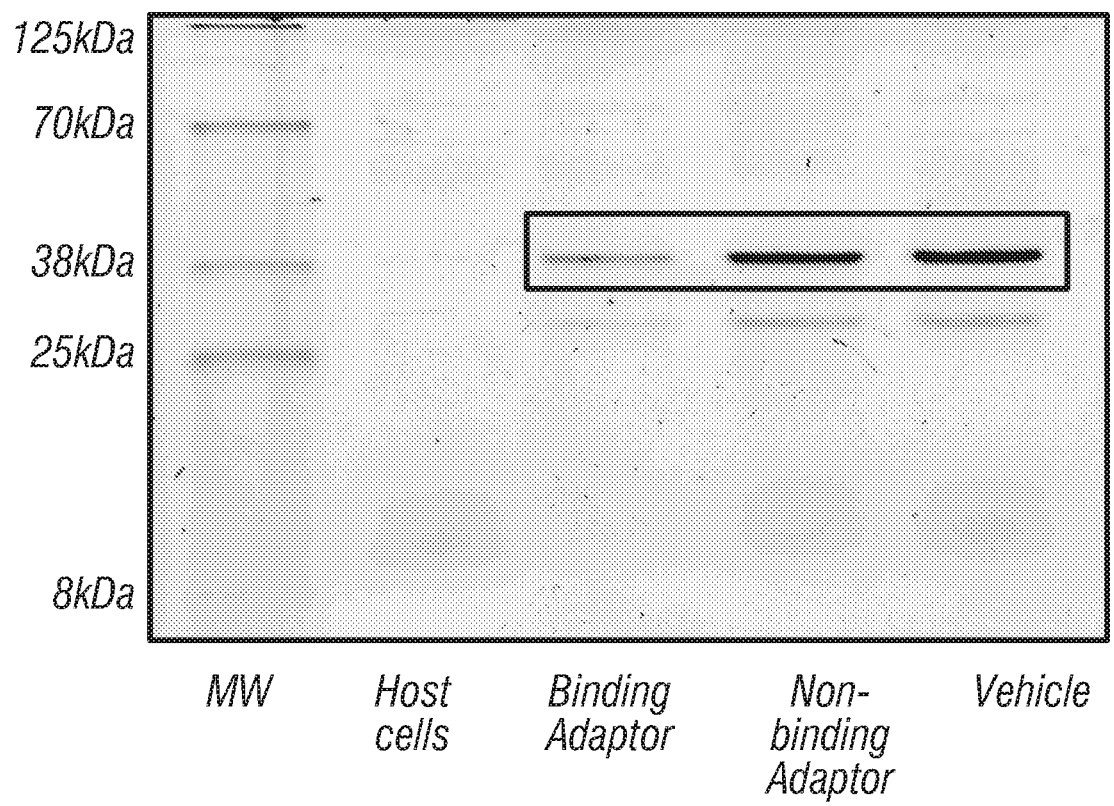
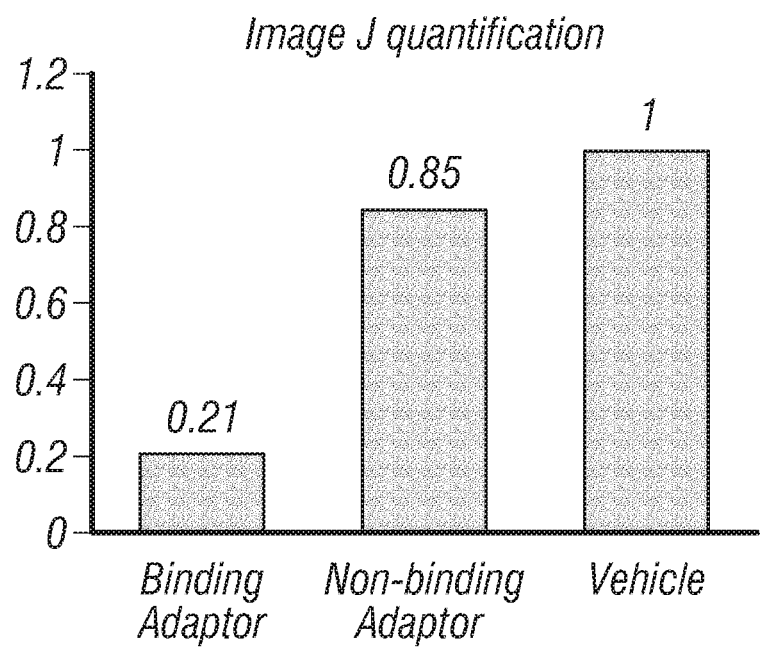
FIG. 6E

FLAG-HA4-hUbL

```
        10         20         30         40         50         60
MDYKDDDDKV SSVPTKLEVV AATPTSLLIS WDAPMSSSSV YYYRITYGET GGNSPVQEFT
    FLAG                   HA4
        70         80         90        100        110        120
VPYSSSTATI SGLSPGVDYT ITVYAWGEDS AGYMFMYSPI SINYRTCGGS GGTQVTLKTL
                  HA4                           hUbL
       130        140        150        160        170        180
QQQTFKIDID PEETVKALKE KIESEKGKDA FPVAGQKLIY AGKILNDDTA LKEYKIDEKN
                           hUbL
       190
FVVVMVTKPK AVSTP
    hUbL
```

Number of amino acids: 195
Molecular weight: 21312.04
Theoretical pI: 4.76

FIG. 7F

FLAG-HA4-hL1-hUbL

```
         10         20         30         40         50         60
MDYKDDDDKV SSVPTKLEVV AATPTSLLIS WDAPMSSSSV YYYRITYGET GGNSPVQEFT
FLAG                             HA4
         70         80         90        100        110        120
VPYSSSTATI SGLSPGVDYT ITVYAWGEDS AGYMFMYSPI SINYRTCVST PAPATTQQSA
                HA4                                            hL1
        130        140        150        160        170        180
PASTTAVTSS TTTTVAQAPT PVPALAPTST PASITPASAT ASSEPAPASA AKQEKPAEKP
                 hL1
        190        200        210        220        230        240
AETPVATSPT ATDSTSGDSS RSNLFEDATS ALVTGQVTLK TLQQTFKID IDPEETVKAL
                 hL1
        250        260        270        280        290
KEKIESEKGK DAFPVAGQKL IYAGKILNDD TALKEYKIDE KNFVVVMVTK PKAVSTP
                                     hUbL                  hUbL
```

Number of amino acids: 297
Molecular weight: 31245.82
Theoretical pI: 4.63

FIG. 7H

FLAG-hUbL-Nsa1

```
        10         20         30         40         50         60
MDYKDDDDKM QVTLKTLQQQ TFKIDIDPEE TVKALKEKIE SEKGKDAFPV AGQKLIYAGK
FLAG                  hUbL
        70         80         90        100        110        120
ILNDDTALKE YKIDEKNFVV VMVTKPKAVS TPGLGLGGVS SVPTKLEVVA ATPTSLLISW
         hUbL                                                Nsa1
       130        140        150        160        170        180
DAPAVTVDYY VITYGETGSG GYAWQEFEVP GSKSTATISG LKPGVDYTIT VYAGYYGYPT
Nsa1
       190
YYSSPISINY RT
Nsa1
```

Number of amino acids: 192
Molecular weight: 21012.83
Theoretical pI: 4.86

FIG. 7J

FLAG-Nsa1-hUbL

```
         10         20         30         40         50         60
MDYKDDDDKV SSVPTKLEVV AATPTSLLIS WDAPAVTVDY YVITTYGETGS GGYAWQEFEV
FLAG                  Nsa1
         70         80         90        100        110        120
PGSKSTATIS GLKPGVDYTI TVYAGYGYP  TYYSSPISIN YRTGGSGGTQ VTLKTLQQQT
           Nsa1                            hUbL
        130        140        150        160        170        180
FKIDIDPEET VKALKEKIES EKGKDAFPVA GQKLIYAGKI LNDDTALKEY KIDEKNFVVV
           hUbL
        190
MVTKPKAVST P
hUbL
```

Number of amino acids: 191
Molecular weight: 20843.50
Theoretical pI: 4.86

FIG. 7K

FLAG-hUbL-hL1-Nsa1

```
         10         20         30         40         50         60
MDYKDDDDKQ VTLKTLQQQT FKIDIDPEET VKALKEKIES EKGKDAFPVA GQKLIYAGKI
FLAG                                  hUbL
         70         80         90        100        110        120
LNDDTALKEY KIDEKNFVVV MVTKPKAVST PAPATTQQSA PASTTAVTSS TTTTVAQAPT
             hUbL                                       hL1
        130        140        150        160        170        180
PVPALAPTST PASITPASAT ASSEPAPASA AKQEKPAEKP AETPVATSPT ATDSTSGDSS
                                hL1
        190        200        210        220        230        240
RSNLFEDATS ALVTGVSSVP TKLEVVAATP TSLLISWDAP AVTVDYYVIT YGETGSGGYA
      hL1                                Nsa1
        250        260        270        280
WQEFEVPGSK STATISGLKP GVDYTITVYA GYYGYPTYYS SPISINYRT
                                Nsa1
```

Number of amino acids: 289
Molecular weight: 30392.86
Theoretical pI: 4.70

*FIG. 7L*

FLAG-Nsa1-hL1-hUbL

```
         10          20          30          40          50          60
     MDYKDDDDKV  SSVPTKLEVV  AATPTSLLIS  WDAPAVTVDY  YVITTYGETGS  GGYAWGEFFV
     FLAG                               Nsa1
         70          80          90         100         110         120
     PGSKSTATIS  GLKPGVDYTI  TVYAGYYGYP  TYYSSPISIN  YRTVSTPAPA  TTQQSAPAST
                    Nsa1                                                hL1
        130         140         150         160         170         180
     TAVTSSTTTT  VAQAPTPVPA  LAPTSTPASI  TPASATASSE  PAPASAAKQE  KPAEKPAETP
                                       hL1
        190         200         210         220         230         240
     VATSPTATDS  TSGDSSRSNL  FEDATSALVT  GQVTLKTLQQ  QTFKIDIDPE  ETVKALKEKI
                hL1                                             hUbL
        250         260         270         280         290
     ESEKGKDAFP  VAGQKLIYAG  KILNDDTALK  EYKIDEKNFV  VVMVTKPKAV  STP
                                   hUbL
```

Number of amino acids: 293  
Molecular weight: 30777.29  
Theoretical pI: 4.70

*FIG. 7M*

FLAG-hUbL-Cs1

```
             10         20         30         40         50         60
     MDYKDDDDKM QVTLKTLQQQ TFKIDIDPEE TVKALKEKIE SEKGKDAFPV AGQKLIYAGK
     FLAG                                    hUbL
             70         80         90        100        110        120
     ILNDDTALKE YKIDEKNFVV VMVTKPKAVS TPGLGLGGVS SVPTKLEVVA ATPTSLLISW
                   hUbL                                         Cs1
            130        140        150        160        170        180
     DAPAVTVDYY VITYGETGYW PYYWQEFEVP GSKSTATISG LKPGVDYTIT VYAGSYDSYY
                                        Cs1
            190
     YYGSPISINY RT
         Cs1
```

Number of amino acids: 192
Molecular weight: 21354.20
Theoretical pI: 4.77

*FIG. 70*

```
                        SEQUENCE LISTING

<160> NUMBER OF SEQ ID NOS: 22

<210> SEQ ID NO 1
<211> LENGTH: 195
<212> TYPE: PRT
<213> ORGANISM: Artificial sequence
<220> FEATURE:
<223> OTHER INFORMATION: Synthetic polypeptide

<400> SEQUENCE: 1

Met Asp Tyr Lys Asp Asp Asp Lys Ala Ser Val Ser Leu Thr Phe
1               5                   10                  15

Lys Asn Phe Lys Lys Glu Lys Val Pro Leu Asp Leu Glu Pro Ser Asn
                20                  25                  30

Thr Ile Leu Glu Thr Lys Thr Lys Leu Ala Gln Ser Ile Ser Cys Glu
            35                  40                  45

Glu Ser Gln Ile Lys Leu Ile Tyr Ser Gly Lys Val Leu Gln Asp Ser
    50                  55                  60

Lys Thr Val Ser Glu Cys Gly Leu Lys Asp Gly Asp Gln Val Val Phe
65                  70                  75                  80

Met Val Ser Gln Lys Lys Ser Gly Gly Ser Gly Gly Thr Met Val Ser
                85                  90                  95

Ser Val Pro Thr Lys Leu Glu Val Val Ala Ala Thr Pro Thr Ser Leu
                100                 105                 110

Leu Ile Ser Trp Asp Ala Pro Met Ser Ser Ser Ser Val Tyr Tyr Tyr
            115                 120                 125

Arg Ile Thr Tyr Gly Glu Thr Gly Gly Asn Ser Pro Val Gln Glu Phe
    130                 135                 140

Thr Val Pro Tyr Ser Ser Ser Thr Ala Thr Ile Ser Gly Leu Ser Pro
145                 150                 155                 160

Gly Val Asp Tyr Thr Ile Thr Val Tyr Ala Trp Gly Glu Asp Ser Ala
                165                 170                 175

Gly Tyr Met Phe Met Tyr Ser Pro Ile Ser Ile Asn Tyr Arg Thr Cys
                180                 185                 190

Leu Glu Tyr
        195

<210> SEQ ID NO 2
<211> LENGTH: 195
<212> TYPE: PRT
<213> ORGANISM: Artificial sequence
<220> FEATURE:
<223> OTHER INFORMATION: Synthetic polypeptide

<400> SEQUENCE: 2

Met Val Ser Ser Val Pro Thr Lys Leu Glu Val Val Ala Ala Thr Pro
1               5                   10                  15

Thr Ser Leu Leu Ile Ser Trp Asp Ala Pro Met Ser Ser Ser Ser Val
                20                  25                  30

Tyr Tyr Tyr Arg Ile Thr Tyr Gly Glu Thr Gly Gly Asn Ser Pro Val
            35                  40                  45

Gln Glu Phe Thr Val Pro Tyr Ser Ser Ser Thr Ala Thr Ile Ser Gly
    50                  55                  60

Leu Ser Pro Gly Val Asp Tyr Thr Ile Thr Val Tyr Ala Trp Gly Glu
```

```
            65                  70                  75                  80
Asp Ser Ala Gly Tyr Met Phe Met Tyr Ser Pro Ile Ser Ile Asn Tyr
                85                  90                  95

Arg Thr Cys Gly Gly Ser Gly Gly Thr Met Val Ser Leu Thr Phe Lys
                100                 105                 110

Asn Phe Lys Lys Glu Lys Val Pro Leu Asp Leu Glu Pro Ser Asn Thr
                115                 120                 125

Ile Leu Glu Thr Lys Thr Lys Leu Ala Gln Ser Ile Ser Cys Glu Glu
            130                 135                 140

Ser Gln Ile Lys Leu Ile Tyr Ser Gly Lys Val Leu Gln Asp Ser Lys
145                 150                 155                 160

Thr Val Ser Glu Cys Gly Leu Lys Asp Gly Asp Gln Val Val Phe Met
                165                 170                 175

Val Ser Gln Lys Lys Ser Ala Ser Asp Tyr Lys Asp Asp Asp Asp Lys
                180                 185                 190

Leu Glu Tyr
        195

<210> SEQ ID NO 3
<211> LENGTH: 260
<212> TYPE: PRT
<213> ORGANISM: Artificial sequence
<220> FEATURE:
<223> OTHER INFORMATION: Synthetic polypeptide

<400> SEQUENCE: 3

Met Val Ser Ser Val Pro Thr Lys Leu Glu Val Val Ala Ala Thr Pro
1               5                   10                  15

Thr Ser Leu Leu Ile Ser Trp Asp Ala Pro Met Ser Ser Ser Ser Val
            20                  25                  30

Tyr Tyr Tyr Arg Ile Thr Tyr Gly Glu Thr Gly Gly Asn Ser Pro Val
                35                  40                  45

Gln Glu Phe Thr Val Pro Tyr Ser Ser Thr Ala Thr Ile Ser Gly
            50                  55                  60

Leu Ser Pro Gly Val Asp Tyr Thr Ile Thr Val Tyr Ala Trp Gly Glu
65                  70                  75                  80

Asp Ser Ala Gly Tyr Met Phe Met Tyr Ser Pro Ile Ser Ile Asn Tyr
                85                  90                  95

Arg Thr Cys Phe Glu Thr Lys Thr Lys Val Thr Glu Pro Pro Ile Ala
                100                 105                 110

Pro Glu Ser Ala Thr Thr Pro Gly Arg Glu Asn Ser Thr Glu Ala Ser
            115                 120                 125

Pro Ser Thr Asp Ala Ser Ala Ala Pro Ala Ala Thr Ala Pro Glu Gly
            130                 135                 140

Ser Gln Pro Gln Glu Glu Gln Thr Ala Thr Thr Glu Arg Thr Glu Ser
145                 150                 155                 160

Ala Ser Thr Pro Gly Phe Val Val Gly Thr Met Val Ser Leu Thr Phe
                165                 170                 175

Lys Asn Phe Lys Lys Glu Lys Val Pro Leu Asp Leu Glu Pro Ser Asn
                180                 185                 190

Thr Ile Leu Glu Thr Lys Thr Lys Leu Ala Gln Ser Ile Ser Cys Glu
            195                 200                 205

Glu Ser Gln Ile Lys Leu Ile Tyr Ser Gly Lys Val Leu Gln Asp Ser
        210                 215                 220

Lys Thr Val Ser Glu Cys Gly Leu Lys Asp Gly Asp Gln Val Val Phe
```

```
                    225                 230                 235                 240

Met Val Ser Gln Lys Lys Ser Ala Ser Asp Tyr Lys Asp Asp Asp
                245                 250                 255

Lys Leu Glu Tyr
            260

<210> SEQ ID NO 4
<211> LENGTH: 256
<212> TYPE: PRT
<213> ORGANISM: Artificial sequence
<220> FEATURE:
<223> OTHER INFORMATION: Synthetic polypeptide

<400> SEQUENCE: 4

Met Asp Tyr Lys Asp Asp Asp Lys Ala Ser Val Ser Leu Thr Phe
1               5                   10                  15

Lys Asn Phe Lys Lys Glu Lys Val Pro Leu Asp Leu Glu Pro Ser Asn
                20                  25                  30

Thr Ile Leu Glu Thr Lys Thr Lys Leu Ala Gln Ser Ile Ser Cys Glu
            35                  40                  45

Glu Ser Gln Ile Lys Leu Ile Tyr Ser Gly Lys Val Leu Gln Asp Ser
        50                  55                  60

Lys Thr Val Ser Glu Cys Gly Leu Lys Asp Gly Asp Gln Val Val Phe
65                  70                  75                  80

Met Val Ser Gln Lys Lys Ser Thr Lys Thr Lys Val Thr Glu Pro Pro
                85                  90                  95

Ile Ala Pro Glu Ser Ala Thr Thr Pro Gly Arg Glu Asn Ser Thr Glu
            100                 105                 110

Ala Ser Pro Ser Thr Asp Ala Ser Ala Ala Pro Ala Ala Thr Ala Pro
        115                 120                 125

Glu Gly Ser Gln Pro Gln Glu Glu Gln Thr Ala Thr Thr Glu Arg Thr
130                 135                 140

Glu Ser Ala Ser Thr Pro Gly Phe Val Gly Val Ser Ser Val Pro
145                 150                 155                 160

Thr Lys Leu Glu Val Val Ala Ala Thr Pro Thr Ser Leu Leu Ile Ser
                165                 170                 175

Trp Asp Ala Pro Met Ser Ser Ser Val Tyr Tyr Arg Ile Thr
            180                 185                 190

Tyr Gly Glu Thr Gly Gly Asn Ser Pro Val Gln Glu Phe Thr Val Pro
        195                 200                 205

Tyr Ser Ser Ser Thr Ala Thr Ile Ser Gly Leu Ser Pro Gly Val Asp
    210                 215                 220

Tyr Thr Ile Thr Val Tyr Ala Trp Gly Glu Asp Ser Ala Gly Tyr Met
225                 230                 235                 240

Phe Met Tyr Ser Pro Ile Ser Ile Asn Tyr Arg Thr Cys Leu Glu Tyr
                245                 250                 255

<210> SEQ ID NO 5
<211> LENGTH: 198
<212> TYPE: PRT
<213> ORGANISM: Artificial sequence
<220> FEATURE:
<223> OTHER INFORMATION: Synthetic polypeptide

<400> SEQUENCE: 5

Met Asp Tyr Lys Asp Asp Asp Lys Met Gln Val Thr Leu Lys Thr
1               5                   10                  15
```

```
Leu Gln Gln Gln Thr Phe Lys Ile Asp Ile Asp Pro Glu Glu Thr Val
         20                  25                  30

Lys Ala Leu Lys Glu Lys Ile Glu Ser Glu Lys Gly Lys Asp Ala Phe
             35                  40                  45

Pro Val Ala Gly Gln Lys Leu Ile Tyr Ala Gly Lys Ile Leu Asn Asp
 50                  55                  60

Asp Thr Ala Leu Lys Glu Tyr Lys Ile Asp Glu Lys Asn Phe Val Val
 65                  70                  75                  80

Val Met Val Thr Lys Pro Lys Ala Val Ser Thr Pro Gly Leu Gly Leu
                 85                  90                  95

Gly Gly Thr Met Val Ser Ser Val Pro Thr Lys Leu Glu Val Val Ala
            100                 105                 110

Ala Thr Pro Thr Ser Leu Leu Ile Ser Trp Asp Ala Pro Met Ser Ser
            115                 120                 125

Ser Ser Val Tyr Tyr Tyr Arg Ile Thr Tyr Gly Glu Thr Gly Gly Asn
        130                 135                 140

Ser Pro Val Gln Glu Phe Thr Val Pro Tyr Ser Ser Ser Thr Ala Thr
145                 150                 155                 160

Ile Ser Gly Leu Ser Pro Gly Val Asp Tyr Thr Ile Thr Val Tyr Ala
                165                 170                 175

Trp Gly Glu Asp Ser Ala Gly Tyr Met Phe Met Tyr Ser Pro Ile Ser
                180                 185                 190

Ile Asn Tyr Arg Thr Cys
                195

<210> SEQ ID NO 6
<211> LENGTH: 195
<212> TYPE: PRT
<213> ORGANISM: Artificial sequence
<220> FEATURE:
<223> OTHER INFORMATION: Synthetic polypeptide

<400> SEQUENCE: 6

Met Asp Tyr Lys Asp Asp Asp Asp Lys Val Ser Ser Val Pro Thr Lys
1               5                   10                  15

Leu Glu Val Val Ala Ala Thr Pro Thr Ser Leu Leu Ile Ser Trp Asp
                20                  25                  30

Ala Pro Met Ser Ser Ser Ser Val Tyr Tyr Tyr Arg Ile Thr Tyr Gly
            35                  40                  45

Glu Thr Gly Gly Asn Ser Pro Val Gln Glu Phe Thr Val Pro Tyr Ser
 50                  55                  60

Ser Ser Thr Ala Thr Ile Ser Gly Leu Ser Pro Gly Val Asp Tyr Thr
 65                  70                  75                  80

Ile Thr Val Tyr Ala Trp Gly Glu Asp Ser Ala Gly Tyr Met Phe Met
                 85                  90                  95

Tyr Ser Pro Ile Ser Ile Asn Tyr Arg Thr Cys Gly Gly Ser Gly Gly
            100                 105                 110

Thr Gln Val Thr Leu Lys Thr Leu Gln Gln Gln Thr Phe Lys Ile Asp
        115                 120                 125

Ile Asp Pro Glu Glu Thr Val Lys Ala Leu Lys Glu Lys Ile Glu Ser
    130                 135                 140

Glu Lys Gly Lys Asp Ala Phe Pro Val Ala Gly Gln Lys Leu Ile Tyr
145                 150                 155                 160

Ala Gly Lys Ile Leu Asn Asp Asp Thr Ala Leu Lys Glu Tyr Lys Ile
                165                 170                 175
```

Asp Glu Lys Asn Phe Val Val Met Val Thr Lys Pro Lys Ala Val
            180                 185                 190

Ser Thr Pro
        195

<210> SEQ ID NO 7
<211> LENGTH: 294
<212> TYPE: PRT
<213> ORGANISM: Artificial sequence
<220> FEATURE:
<223> OTHER INFORMATION: Synthetic polypeptide

<400> SEQUENCE: 7

Met Asp Tyr Lys Asp Asp Asp Lys Met Gln Val Thr Leu Lys Thr
1               5                   10                  15

Leu Gln Gln Gln Thr Phe Lys Ile Asp Ile Asp Pro Glu Glu Thr Val
                20                  25                  30

Lys Ala Leu Lys Glu Lys Ile Glu Ser Glu Lys Gly Lys Asp Ala Phe
            35                  40                  45

Pro Val Ala Gly Gln Lys Leu Ile Tyr Ala Gly Lys Ile Leu Asn Asp
50                  55                  60

Asp Thr Ala Leu Lys Glu Tyr Lys Ile Asp Glu Lys Asn Phe Val Val
65                      70                  75                      80

Val Met Val Thr Lys Pro Lys Ala Val Ser Thr Pro Ala Pro Ala Thr
                85                  90                  95

Thr Gln Gln Ser Ala Pro Ala Ser Thr Thr Ala Val Thr Ser Ser Thr
                100                 105                 110

Thr Thr Thr Val Ala Gln Ala Pro Thr Pro Val Pro Ala Leu Ala Pro
            115                 120                 125

Thr Ser Thr Pro Ala Ser Ile Thr Pro Ala Ser Ala Thr Ala Ser Ser
130                 135                 140

Glu Pro Ala Pro Ala Ser Ala Ala Lys Gln Glu Lys Pro Ala Glu Lys
145                 150                 155                 160

Pro Ala Glu Thr Pro Val Ala Thr Ser Pro Thr Ala Thr Asp Ser Thr
                165                 170                 175

Ser Gly Asp Ser Ser Arg Ser Asn Leu Phe Glu Asp Ala Thr Ser Ala
            180                 185                 190

Leu Val Thr Gly Val Ser Ser Val Pro Thr Lys Leu Glu Val Val Ala
            195                 200                 205

Ala Thr Pro Thr Ser Leu Leu Ile Ser Trp Asp Ala Pro Met Ser Ser
210                 215                 220

Ser Ser Val Tyr Tyr Tyr Arg Ile Thr Tyr Gly Glu Thr Gly Gly Asn
225                 230                 235                 240

Ser Pro Val Gln Glu Phe Thr Val Pro Tyr Ser Ser Ser Thr Ala Thr
                245                 250                 255

Ile Ser Gly Leu Ser Pro Gly Val Asp Tyr Thr Ile Thr Val Tyr Ala
            260                 265                 270

Trp Gly Glu Asp Ser Ala Gly Tyr Met Phe Met Tyr Ser Pro Ile Ser
            275                 280                 285

Ile Asn Tyr Arg Thr Cys
        290

<210> SEQ ID NO 8
<211> LENGTH: 297
<212> TYPE: PRT
<213> ORGANISM: Artificial sequence
<220> FEATURE:

<223> OTHER INFORMATION: Synthetic polypeptide

<400> SEQUENCE: 8

Met Asp Tyr Lys Asp Asp Asp Lys Val Ser Ser Val Pro Thr Lys
1               5                   10                  15

Leu Glu Val Val Ala Ala Thr Pro Thr Ser Leu Leu Ile Ser Trp Asp
            20                  25                  30

Ala Pro Met Ser Ser Ser Ser Val Tyr Tyr Tyr Arg Ile Thr Tyr Gly
        35                  40                  45

Glu Thr Gly Gly Asn Ser Pro Val Gln Glu Phe Thr Val Pro Tyr Ser
    50                  55                  60

Ser Ser Thr Ala Thr Ile Ser Gly Leu Ser Pro Gly Val Asp Tyr Thr
65                  70                  75                  80

Ile Thr Val Tyr Ala Trp Gly Glu Asp Ser Ala Gly Tyr Met Phe Met
                85                  90                  95

Tyr Ser Pro Ile Ser Ile Asn Tyr Arg Thr Cys Val Ser Thr Pro Ala
            100                 105                 110

Pro Ala Thr Thr Gln Gln Ser Ala Pro Ala Ser Thr Thr Ala Val Thr
        115                 120                 125

Ser Ser Thr Thr Thr Thr Val Ala Gln Ala Pro Thr Pro Val Pro Ala
    130                 135                 140

Leu Ala Pro Thr Ser Thr Pro Ala Ser Ile Thr Pro Ala Ser Ala Thr
145                 150                 155                 160

Ala Ser Ser Glu Pro Ala Pro Ala Ser Ala Ala Lys Gln Glu Lys Pro
                165                 170                 175

Ala Glu Lys Pro Ala Glu Thr Pro Val Ala Thr Ser Pro Thr Ala Thr
            180                 185                 190

Asp Ser Thr Ser Gly Asp Ser Ser Arg Ser Asn Leu Phe Glu Asp Ala
        195                 200                 205

Thr Ser Ala Leu Val Thr Gly Gln Val Thr Leu Lys Thr Leu Gln Gln
    210                 215                 220

Gln Thr Phe Lys Ile Asp Ile Asp Pro Glu Glu Thr Val Lys Ala Leu
225                 230                 235                 240

Lys Glu Lys Ile Glu Ser Glu Lys Gly Lys Asp Ala Phe Pro Val Ala
                245                 250                 255

Gly Gln Lys Leu Ile Tyr Ala Gly Lys Ile Leu Asn Asp Asp Thr Ala
            260                 265                 270

Leu Lys Glu Tyr Lys Ile Asp Glu Lys Asn Phe Val Val Val Met Val
        275                 280                 285

Thr Lys Pro Lys Ala Val Ser Thr Pro
    290                 295

<210> SEQ ID NO 9
<211> LENGTH: 187
<212> TYPE: PRT
<213> ORGANISM: Artificial sequence
<220> FEATURE:
<223> OTHER INFORMATION: Synthetic polypeptide

<400> SEQUENCE: 9

Met Asp Tyr Lys Asp Asp Asp Lys Ala Ser Val Ser Leu Thr Phe
1               5                   10                  15

Lys Asn Phe Lys Lys Glu Lys Val Pro Leu Asp Leu Glu Pro Ser Asn
            20                  25                  30

Thr Ile Leu Glu Thr Lys Thr Lys Leu Ala Gln Ser Ile Ser Cys Glu
        35                  40                  45

Glu Ser Gln Ile Lys Leu Ile Tyr Ser Gly Lys Val Leu Gln Asp Ser
        50                  55                  60

Lys Thr Val Ser Glu Cys Gly Leu Lys Asp Gly Asp Gln Val Val Phe
 65                  70                  75                  80

Met Val Ser Gln Lys Lys Ser Gly Gly Ser Gly Gly Thr Val Ser Ser
                 85                  90                  95

Val Pro Thr Lys Leu Glu Val Val Ala Ala Thr Pro Thr Ser Leu Leu
                100                 105                 110

Ile Ser Trp Asp Ala Pro Ala Val Thr Val Asp Tyr Tyr Val Ile Thr
            115                 120                 125

Tyr Gly Glu Thr Gly Ser Gly Tyr Ala Trp Gln Glu Phe Glu Val
        130                 135                 140

Pro Gly Ser Lys Ser Thr Ala Thr Ile Ser Gly Leu Lys Pro Gly Val
145                 150                 155                 160

Asp Tyr Thr Ile Thr Val Tyr Ala Gly Tyr Tyr Gly Tyr Pro Thr Tyr
                165                 170                 175

Tyr Ser Ser Pro Ile Ser Ile Asn Tyr Arg Thr
            180                 185

<210> SEQ ID NO 10
<211> LENGTH: 192
<212> TYPE: PRT
<213> ORGANISM: Artificial sequence
<220> FEATURE:
<223> OTHER INFORMATION: Synthetic polypeptide

<400> SEQUENCE: 10

Met Asp Tyr Lys Asp Asp Asp Lys Met Gln Val Thr Leu Lys Thr
 1               5                  10                  15

Leu Gln Gln Gln Thr Phe Lys Ile Asp Ile Asp Pro Glu Glu Thr Val
                 20                  25                  30

Lys Ala Leu Lys Glu Lys Ile Glu Ser Glu Lys Gly Lys Asp Ala Phe
             35                  40                  45

Pro Val Ala Gly Gln Lys Leu Ile Tyr Ala Gly Lys Ile Leu Asn Asp
 50                  55                  60

Asp Thr Ala Leu Lys Glu Tyr Lys Ile Asp Glu Lys Asn Phe Val Val
 65                  70                  75                  80

Val Met Val Thr Lys Pro Lys Ala Val Ser Thr Pro Gly Leu Gly Leu
                 85                  90                  95

Gly Gly Val Ser Ser Val Pro Thr Lys Leu Glu Val Val Ala Ala Thr
            100                 105                 110

Pro Thr Ser Leu Leu Ile Ser Trp Asp Ala Pro Ala Val Thr Val Asp
        115                 120                 125

Tyr Tyr Val Ile Thr Tyr Gly Glu Thr Gly Ser Gly Tyr Ala Trp
    130                 135                 140

Gln Glu Phe Glu Val Pro Gly Ser Lys Ser Thr Ala Thr Ile Ser Gly
145                 150                 155                 160

Leu Lys Pro Gly Val Asp Tyr Thr Ile Thr Val Tyr Ala Gly Tyr Tyr
                165                 170                 175

Gly Tyr Pro Thr Tyr Tyr Ser Ser Pro Ile Ser Ile Asn Tyr Arg Thr
            180                 185                 190

<210> SEQ ID NO 11
<211> LENGTH: 191
<212> TYPE: PRT
<213> ORGANISM: Artificial sequence
<220> FEATURE:
<223> OTHER INFORMATION: Synthetic polypeptide

<400> SEQUENCE: 11

Met Asp Tyr Lys Asp Asp Asp Lys Val Ser Ser Val Pro Thr Lys
1               5                   10                  15

Leu Glu Val Val Ala Ala Thr Pro Thr Ser Leu Leu Ile Ser Trp Asp
            20                  25                  30

Ala Pro Ala Val Thr Val Asp Tyr Tyr Val Ile Thr Tyr Gly Glu Thr
        35                  40                  45

Gly Ser Gly Gly Tyr Ala Trp Gln Glu Phe Glu Val Pro Gly Ser Lys
    50                  55                  60

Ser Thr Ala Thr Ile Ser Gly Leu Lys Pro Gly Val Asp Tyr Thr Ile
65                  70                  75                  80

Thr Val Tyr Ala Gly Tyr Tyr Gly Tyr Pro Thr Tyr Tyr Ser Ser Pro
                85                  90                  95

Ile Ser Ile Asn Tyr Arg Thr Gly Gly Ser Gly Gly Thr Gln Val Thr
            100                 105                 110

Leu Lys Thr Leu Gln Gln Gln Thr Phe Lys Ile Asp Ile Asp Pro Glu
        115                 120                 125

Glu Thr Val Lys Ala Leu Lys Glu Lys Ile Glu Ser Glu Lys Gly Lys
    130                 135                 140

Asp Ala Phe Pro Val Ala Gly Gln Lys Leu Ile Tyr Ala Gly Lys Ile
145                 150                 155                 160

Leu Asn Asp Asp Thr Ala Leu Lys Glu Tyr Lys Ile Asp Glu Lys Asn
                165                 170                 175

Phe Val Val Val Met Val Thr Lys Pro Lys Ala Val Ser Thr Pro
            180                 185                 190

<210> SEQ ID NO 12
<211> LENGTH: 289
<212> TYPE: PRT
<213> ORGANISM: Artificial sequence
<220> FEATURE:
<223> OTHER INFORMATION: Synthetic polypeptide

<400> SEQUENCE: 12

Met Asp Tyr Lys Asp Asp Asp Lys Gln Val Thr Leu Lys Thr Leu
1               5                   10                  15

Gln Gln Gln Thr Phe Lys Ile Asp Ile Asp Pro Glu Glu Thr Val Lys
            20                  25                  30

Ala Leu Lys Glu Lys Ile Glu Ser Glu Lys Gly Lys Asp Ala Phe Pro
        35                  40                  45

Val Ala Gly Gln Lys Leu Ile Tyr Ala Gly Lys Ile Leu Asn Asp Asp
    50                  55                  60

Thr Ala Leu Lys Glu Tyr Lys Ile Asp Glu Lys Asn Phe Val Val Val
65                  70                  75                  80

Met Val Thr Lys Pro Lys Ala Val Ser Thr Pro Ala Pro Ala Thr Thr
                85                  90                  95

Gln Gln Ser Ala Pro Ala Ser Thr Thr Ala Val Thr Ser Ser Thr Thr
            100                 105                 110

Thr Thr Val Ala Gln Ala Pro Thr Pro Val Pro Ala Leu Ala Pro Thr
        115                 120                 125

Ser Thr Pro Ala Ser Ile Thr Pro Ala Ser Ala Thr Ala Ser Ser Glu
    130                 135                 140

Pro Ala Pro Ala Ser Ala Ala Lys Gln Glu Lys Pro Ala Glu Lys Pro

```
                145                 150                 155                 160
Ala Glu Thr Pro Val Ala Thr Ser Pro Thr Ala Thr Asp Ser Thr Ser
                    165                 170                 175
Gly Asp Ser Ser Arg Ser Asn Leu Phe Glu Asp Ala Thr Ser Ala Leu
            180                 185                 190
Val Thr Gly Val Ser Ser Val Pro Thr Lys Leu Glu Val Val Ala Ala
        195                 200                 205
Thr Pro Thr Ser Leu Leu Ile Ser Trp Asp Ala Pro Ala Val Thr Val
    210                 215                 220
Asp Tyr Tyr Val Ile Thr Tyr Gly Glu Thr Gly Ser Gly Gly Tyr Ala
225                 230                 235                 240
Trp Gln Glu Phe Glu Val Pro Gly Ser Lys Ser Thr Ala Thr Ile Ser
                245                 250                 255
Gly Leu Lys Pro Gly Val Asp Tyr Thr Ile Thr Val Tyr Ala Gly Tyr
            260                 265                 270
Tyr Gly Tyr Pro Thr Tyr Tyr Ser Ser Pro Ile Ser Ile Asn Tyr Arg
        275                 280                 285
Thr

<210> SEQ ID NO 13
<211> LENGTH: 293
<212> TYPE: PRT
<213> ORGANISM: Artificial sequence
<220> FEATURE:
<223> OTHER INFORMATION: Synthetic polypeptide

<400> SEQUENCE: 13

Met Asp Tyr Lys Asp Asp Asp Lys Val Ser Ser Val Pro Thr Lys
1               5                   10                  15
Leu Glu Val Val Ala Ala Thr Pro Thr Ser Leu Leu Ile Ser Trp Asp
                20                  25                  30
Ala Pro Ala Val Thr Val Asp Tyr Tyr Val Ile Thr Tyr Gly Glu Thr
            35                  40                  45
Gly Ser Gly Gly Tyr Ala Trp Gln Glu Phe Glu Val Pro Gly Ser Lys
        50                  55                  60
Ser Thr Ala Thr Ile Ser Gly Leu Lys Pro Gly Val Asp Tyr Thr Ile
65                  70                  75                  80
Thr Val Tyr Ala Gly Tyr Tyr Gly Tyr Pro Thr Tyr Tyr Ser Ser Pro
                85                  90                  95
Ile Ser Ile Asn Tyr Arg Thr Val Ser Thr Pro Ala Pro Ala Thr Thr
            100                 105                 110
Gln Gln Ser Ala Pro Ala Ser Thr Thr Ala Val Thr Ser Ser Thr Thr
        115                 120                 125
Thr Thr Val Ala Gln Ala Pro Thr Pro Val Pro Ala Leu Ala Pro Thr
    130                 135                 140
Ser Thr Pro Ala Ser Ile Thr Pro Ala Ser Ala Thr Ala Ser Ser Glu
145                 150                 155                 160
Pro Ala Pro Ala Ser Ala Ala Lys Gln Glu Lys Pro Ala Glu Lys Pro
                165                 170                 175
Ala Glu Thr Pro Val Ala Thr Ser Pro Thr Ala Thr Asp Ser Thr Ser
            180                 185                 190
Gly Asp Ser Ser Arg Ser Asn Leu Phe Glu Asp Ala Thr Ser Ala Leu
        195                 200                 205
Val Thr Gly Gln Val Thr Leu Lys Thr Leu Gln Gln Gln Thr Phe Lys
    210                 215                 220
```

Ile Asp Ile Asp Pro Glu Glu Thr Val Lys Ala Leu Lys Glu Lys Ile
225                 230                 235                 240

Glu Ser Glu Lys Gly Lys Asp Ala Phe Pro Val Ala Gly Gln Lys Leu
            245                 250                 255

Ile Tyr Ala Gly Lys Ile Leu Asn Asp Asp Thr Ala Leu Lys Glu Tyr
        260                 265                 270

Lys Ile Asp Glu Lys Asn Phe Val Val Met Val Thr Lys Pro Lys
    275                 280                 285

Ala Val Ser Thr Pro
    290

<210> SEQ ID NO 14
<211> LENGTH: 190
<212> TYPE: PRT
<213> ORGANISM: Artificial sequence
<220> FEATURE:
<223> OTHER INFORMATION: Synthetic polypeptide

<400> SEQUENCE: 14

Met Asp Tyr Lys Asp Asp Asp Lys Ala Ser Val Ser Leu Thr Phe
1               5                   10                  15

Lys Asn Phe Lys Lys Glu Lys Val Pro Leu Asp Leu Glu Pro Ser Asn
                20                  25                  30

Thr Ile Leu Glu Thr Lys Thr Lys Leu Ala Gln Ser Ile Ser Cys Glu
            35                  40                  45

Glu Ser Gln Ile Lys Leu Ile Tyr Ser Gly Lys Val Leu Gln Asp Ser
        50                  55                  60

Lys Thr Val Ser Glu Cys Gly Leu Lys Asp Gly Asp Gln Val Val Phe
65                  70                  75                  80

Met Val Ser Gln Lys Lys Ser Gly Gly Ser Gly Gly Thr Met Val Ser
                85                  90                  95

Ser Val Pro Thr Lys Leu Glu Val Val Ala Ala Thr Pro Thr Ser Leu
                100                 105                 110

Leu Ile Ser Trp Asp Ala Pro Ala Val Thr Val Asp Tyr Tyr Val Ile
            115                 120                 125

Thr Tyr Gly Glu Thr Gly Tyr Trp Pro Tyr Tyr Trp Gln Glu Phe Glu
        130                 135                 140

Val Pro Gly Ser Lys Ser Thr Ala Thr Ile Ser Gly Leu Lys Pro Gly
145                 150                 155                 160

Val Asp Tyr Thr Ile Thr Val Tyr Ala Gly Ser Tyr Asp Ser Tyr Tyr
                165                 170                 175

Tyr Tyr Gly Ser Cys Ser Pro Ile Ser Ile Asn Tyr Arg Thr
                180                 185                 190

<210> SEQ ID NO 15
<211> LENGTH: 192
<212> TYPE: PRT
<213> ORGANISM: Artificial sequence
<220> FEATURE:
<223> OTHER INFORMATION: Synthetic polypeptide

<400> SEQUENCE: 15

Met Asp Tyr Lys Asp Asp Asp Lys Met Gln Val Thr Leu Lys Thr
1               5                   10                  15

Leu Gln Gln Gln Thr Phe Lys Ile Asp Ile Asp Pro Glu Glu Thr Val
                20                  25                  30

Lys Ala Leu Lys Glu Lys Ile Glu Ser Glu Lys Gly Lys Asp Ala Phe

```
               35                  40                  45
Pro Val Ala Gly Gln Lys Leu Ile Tyr Ala Gly Lys Ile Leu Asn Asp
            50                  55                  60
Asp Thr Ala Leu Lys Glu Tyr Lys Ile Asp Glu Lys Asn Phe Val Val
 65                  70                  75                  80
Val Met Val Thr Lys Pro Lys Ala Val Ser Thr Pro Gly Leu Gly Leu
                85                  90                  95
Gly Gly Val Ser Ser Val Pro Thr Lys Leu Glu Val Val Ala Ala Thr
           100                 105                 110
Pro Thr Ser Leu Leu Ile Ser Trp Asp Ala Pro Ala Val Thr Val Asp
           115                 120                 125
Tyr Tyr Val Ile Thr Tyr Gly Glu Thr Gly Tyr Trp Pro Tyr Tyr Trp
           130                 135                 140
Gln Glu Phe Glu Val Pro Gly Ser Lys Ser Thr Ala Thr Ile Ser Gly
145                 150                 155                 160
Leu Lys Pro Gly Val Asp Tyr Thr Ile Thr Val Tyr Ala Gly Ser Tyr
                165                 170                 175
Asp Ser Tyr Tyr Tyr Tyr Gly Ser Pro Ile Ser Ile Asn Tyr Arg Thr
           180                 185                 190
```

<210> SEQ ID NO 16
<211> LENGTH: 13
<212> TYPE: PRT
<213> ORGANISM: Artificial sequence
<220> FEATURE:
<223> OTHER INFORMATION: Synthetic peptide

<400> SEQUENCE: 16

```
Gly Arg Lys Lys Arg Arg Gln Arg Arg Pro Pro Gln
1               5                   10
```

<210> SEQ ID NO 17
<211> LENGTH: 16
<212> TYPE: PRT
<213> ORGANISM: Artificial sequence
<220> FEATURE:
<223> OTHER INFORMATION: Synthetic peptide

<400> SEQUENCE: 17

```
Arg Gln Ile Lys Ile Trp Phe Gln Asn Arg Arg Met Lys Trp Lys Lys
1               5                   10                  15
```

<210> SEQ ID NO 18
<211> LENGTH: 26
<212> TYPE: PRT
<213> ORGANISM: Artificial sequence
<220> FEATURE:
<223> OTHER INFORMATION: Synthetic peptide

<400> SEQUENCE: 18

```
Gly Ile Gly Ala Val Leu Lys Val Leu Thr Thr Gly Leu Pro Ala Leu
1               5                   10                  15
Ile Ser Trp Ile Lys Arg Lys Arg Gln Gln
            20                  25
```

<210> SEQ ID NO 19
<211> LENGTH: 10
<212> TYPE: PRT
<213> ORGANISM: Artificial sequence
<220> FEATURE:
<223> OTHER INFORMATION: Synthetic peptide

```
<400> SEQUENCE: 19

Thr Lys Ile Glu Ser Leu Lys Glu His Gly
1               5                   10

<210> SEQ ID NO 20
<211> LENGTH: 10
<212> TYPE: PRT
<213> ORGANISM: Artificial sequence
<220> FEATURE:
<223> OTHER INFORMATION: Synthetic peptide

<400> SEQUENCE: 20

Thr Gln Ile Glu Asn Leu Lys Glu Lys Gly
1               5                   10

<210> SEQ ID NO 21
<211> LENGTH: 26
<212> TYPE: PRT
<213> ORGANISM: Artificial sequence
<220> FEATURE:
<223> OTHER INFORMATION: Synthetic peptide

<400> SEQUENCE: 21

Ala Ala Leu Glu Ala Leu Ala Glu Ala Leu Glu Ala Leu Ala Glu Ala
1               5                   10                  15

Leu Glu Ala Leu Ala Glu Ala Ala Ala Ala
            20                  25

<210> SEQ ID NO 22
<211> LENGTH: 25
<212> TYPE: PRT
<213> ORGANISM: Artificial sequence
<220> FEATURE:
<223> OTHER INFORMATION: Synthetic peptide

<400> SEQUENCE: 22

Gly Leu Phe Glu Ala Ile Glu Gly Phe Ile Glu Asn Gly Trp Glu Gly
1               5                   10                  15

Met Ile Glu Gly Trp Tyr Gly Cys Gly
            20                  25
```

TARGETING PROTEINS FOR DEGRADATION

This application is a national phase application under 35 U.S.C. § 371 of International Application No. PCT/US2016/060787, filed Nov. 7, 2016, which claims the benefit of United States Provisional Patent Application No. 62/252,472, filed Nov. 7, 2015, the entirety of which is incorporated herein by reference.

This invention was made with government support under Grant No. R01 GM063004 and R21 CA196456 awarded by the National Institutes of Health. The government has certain rights in the invention.

INCORPORATION OF SEQUENCE LISTING

The sequence listing that is contained in the file named "UTFBP1057WO_SeqListing.txt", which is 33 KB (as measured in Microsoft Windows®) and was created on Nov. 4, 2016, is filed herewith by electronic submission and is incorporated by reference herein.

BACKGROUND OF THE INVENTION

1. Field of the Invention

The present invention relates generally to the field of molecular biology and medicine. More particularly, it concerns methods for selectively degrading target proteins, such as proteins involved in disease.

2. Description of Related Art

There are at least four reasons to remove a protein from cells: 1) to determine the function of a protein as part of biomedical research; 2) to validate a therapeutic target; 3) to stop the action of a disease-causing proteins, such as an oncoprotein or a protein causing neurodegeneration; 4) to enhance degradation a protein that accumulates during aging. The current state-of-the-art methodology for controlling cellular protein concentrations is to reduce protein synthesis using RNA interference (RNAi). RNAi technology is based on small RNA molecules that basepair to specific messenger RNAs to inhibit their translation or induce their hydrolysis. This method is well-understood and can be implemented broadly[1].

While RNAi has proven to be a powerful tool and revolutionized experimental biology, it also has several disadvantages. For one, inhibiting protein synthesis means that protein depletion depends on the target's intrinsic degradation rate. Naturally long-lived proteins are difficult to deplete with RNAi, requiring several days of repeated application to decrease protein concentration by more than 50% of the original protein population. Also, RNAi cannot distinguish between different forms of post-translational modification (PTM) on proteins. Another complication is the challenge of delivering highly charged RNA agents into cells. When implemented as a research tool, RNAi precursors are typically transfected directly into cells by lentivirus infection, which can overload the cellular RNA processing machinery and lead to pleiotropic side effects[2,3]. The delivery challenge has largely prevented therapeutic use of RNAi.

SUMMARY OF THE INVENTION

In a first embodiment, the present disclosure provides a recombinant polypeptide comprising a proteasome-binding domain (e.g., a ubiquitin-like domain) and a target-binding domain, wherein said target binding domain specifically binds to a target polypeptide. In some aspects, target polypeptide is a mammalian polypeptide. In certain aspects, the target polypeptide is an intracellular mammalian polypeptide.

In certain aspects, the target polypeptide is a polypeptide associated with a disease or with aging. In some aspects, the target polypeptide is not a reporter protein. In certain aspects, the target-binding domain does not bind to the Huntingtin protein (HTT). In other aspects, the target-binding domain does not bind to protein having a poly-Q sequence.

In some aspects, the target-binding domain is positioned N-terminally relative to the proteasome-binding domain. In other aspects, the target-binding domain is positioned C-terminally relative to the proteasome-binding domain. For example, the proteasome-binding domain comprises a domain from HPV E7, gankyrin, Rad 23 or Rad23b. In certain aspects, the proteasome-binding domain comprises a domain from human protein. For example, the proteasome-binding domain comprises a domain from human Rad23b. In particular, the proteasome-binding domain comprises amino acids 1-83 of human Rad23b. In still further aspects, the proteasome-binding domain can be from a yeast Rad23 (e.g., amino acids 1-77 of yeast Rad23).

In some aspects, the target-binding domain and the proteasome-binding domain are separated by a linker. In certain aspects, the linker is a sequence from Rad23b. In still further aspects, a polypeptide of the embodiments further comprises a cell penetrating peptide (CPP) sequence or a cellular receptor-binding sequence (e.g., for receptor mediated cell penetration). For example, in some aspects, a cellular receptor-binding sequence can be a portion of the sequence of a ligand for the cellular receptor. In some aspects, the CPP sequence (or the cellular receptor-binding sequence) can be positioned N-terminally relative to the target binding domain and/or the proteasome-binding domain. In further aspects, the CPP sequence (or cellular receptor-binding sequence) can be positioned C-terminally relative to the target-binding domain and/or the proteasome-binding domain.

In further aspects, the target-binding domain comprises a monobody or scFv, or another antibody derivative, or a designed or evolved affinity domain that binds to a polypeptide. For example, the target-binding domain comprises the HA4 monobody, the Nsa1 monobody, and/or the Cs1 monobody.

In certain aspects, the target-binding domain binds to a prion, a viral polypeptide, a cellular polypeptide having a disease-associated mutation or the product of an oncogene. In other aspects, the target-binding domain binds to the product of an oncogene. For example, the oncogene is Abl and/or Shp2. In particular, the target-binding domain binds to the SH2 domain of Abl, the N-terminal SH2 domain of Shp2, and/or the C-terminal SH2 domain of Shp2. In some aspects, the target-binding domain binds to misfolded beta-amyloid. In some aspects the target-binding domain recognizes a post-translationally modified protein.

In a further embodiment, there is provided a nucleic acid molecule encoding the polypeptide provided herein comprising a target-binding domain and a proteasome-binding domain, wherein said target-binding domain specifically binds to a target polypeptide. In some aspects, the nucleic acid molecule is a DNA. In other aspects, the nucleic acid molecule is a RNA.

In another embodiment, there is provided an expression vector comprising a sequence encoding the polypeptide provided herein, operably linked to a promoter. In some aspects, the promoter is an inducible or a repressible promoter. In other aspects, the promoter is a tissue or cell type specific promoter. In certain aspects, the vector is a plasmid, a viral vector or an episomal vector. In further aspects, the expression vector further comprises an inducible expression cassette for a suicide gene.

In a further embodiments, there is provided a pharmaceutical composition comprising a polypeptide provided herein the polypeptide comprising a target-binding domain and a proteasome-binding domain, wherein said target-binding domain specifically binds to a target polypeptide. In further aspects, there is provided aa vector comprising a nucleic acid sequence encoding a polypeptide of the embodiments.

In an even further embodiment, there is provided a method of treating a subject having a disease comprising administering an effective amount of the pharmaceutical composition provided herein, wherein said target-binding domain of the polypeptide in the pharmaceutical composition (or encoded by the vector in the pharmaceutical composition) binds to a polypeptide associate with the disease.

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is therefore well below 0.01%. Most preferred is a composition in which no amount of the specified component can be detected with standard analytical methods.

As used herein the specification, "a" or "an" may mean one or more. As used herein in the claim(s), when used in conjunction with the word "comprising," the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 2: Scheme showing the four types of proteasome adaptors or degradons and one model substrate. UbL: ubiquitin-like domain; monobody: the monobody HA4; linker: linker sequence derived from Rad23 or Rad23b; SH2: SH2 domain of c-Abl; GFP: green fluorescent protein.

FIGS. 3A-3C: Degradon leads to substrate degradation in a dose-dependent manner in vitro. (A) Schematic of substrate (SH2-GFP-tail) with the best degradon (yUbL-mB$^{HA4}$). (B) Degradation curves are of 25 nM substrate with varying concentrations of degradon as measured by fluorescence. (C) Substrate degradation was measured by SDS-PAGE and Typhoon at various time points (top). Graphical representation of ImageJ quantification for each time point (bottom).

FIGS. 6A-6G: Degradon transfection leads to substrate degradation in HEK293 cells. (A) Schematic of constructs used in mammalian cells. (B) Fluorescence activated cell sorter (FACS) live cell data represented by dot-plots of GFP fluorescence vs. mCherry fluorescence (arbitrary units) for both non-binding and binding adaptors or degradons. Vertical line represents the center of the untransfected cells; boxes show data used in (C) and (D). (C) Histogram overlays of GFP fluorescence (arbitrary units) of both binding and non-binding adaptors or degradons. Left line is binding adaptor or degradon (corresponding to right box in (B)), right line is non-binding adaptor or degradon (corresponding to left box in (B)). (D) Graphical representation of median GFP fluorescence of non-binding and binding adaptors or degradons, respectively. (E) GFP fluorescence was measured in cell lysates on a gel using the Typhoon (left). Lane 1+ is vehicle-transfected host cells (no integration); lanes 2-4 contain substrate-integrated cells transfected with binding, non-binding, and no adaptor or degradon, respectively. Graphical representation of ImageJ quantification for boxed portion of each lane (right). (F) Left, histogram overlays of GFP fluorescence (arbitrary units) of both binding and non-binding adaptors in N-SH2$^{Shp2}$-GFP-35ΔK stable cells. Right, graphical representation of median GFP fluorescence of non-binding and binding adaptors, respectively. (G) Left, histogram overlays of GFP fluorescence (arbitrary units) of both binding and non-binding adaptors in C-SH2$^{Shp2}$-GFP-35ΔK stable cells. Right, graphical representation of median GFP fluorescence of non-binding and binding adaptors, respectively.

11; 7L=SEQ ID NO: 12; 7M=SEQ ID NO: 13; 7N=SEQ ID NO: 14; 7O=SEQ ID NO: 15)

Figure 8A:
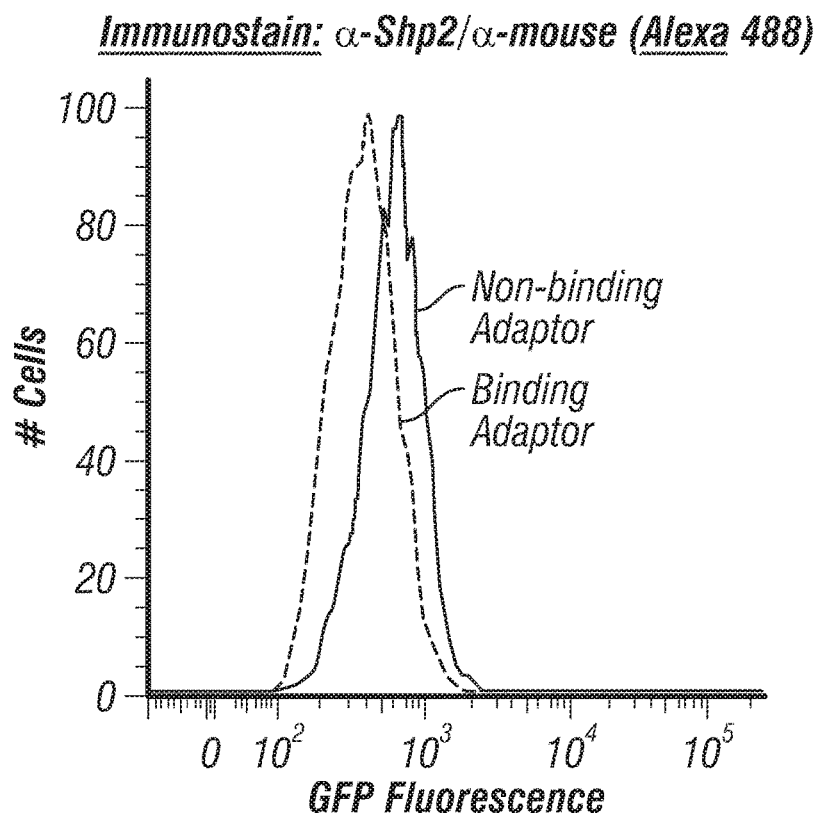
Figure 8B:
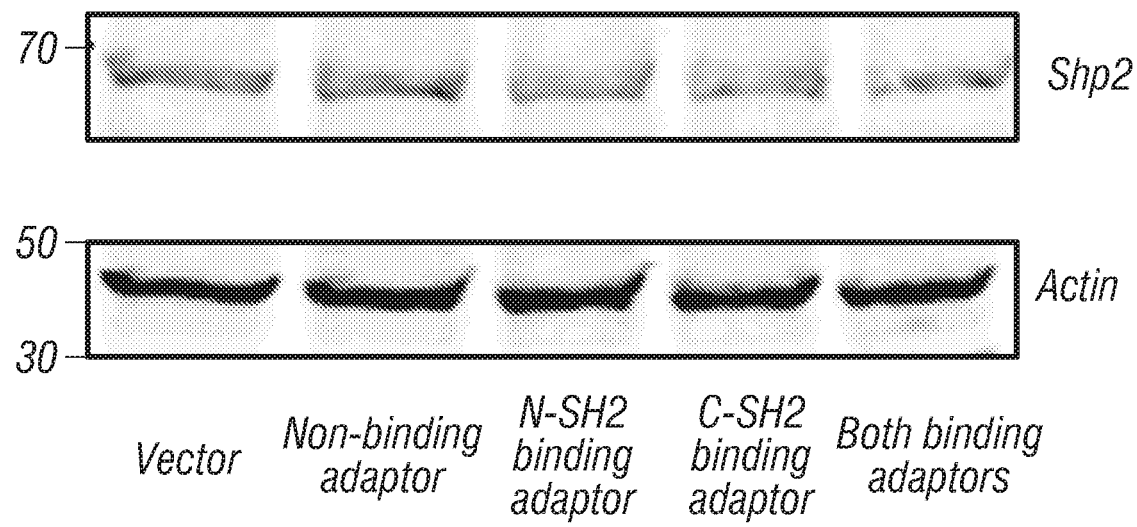
Figure 8C:
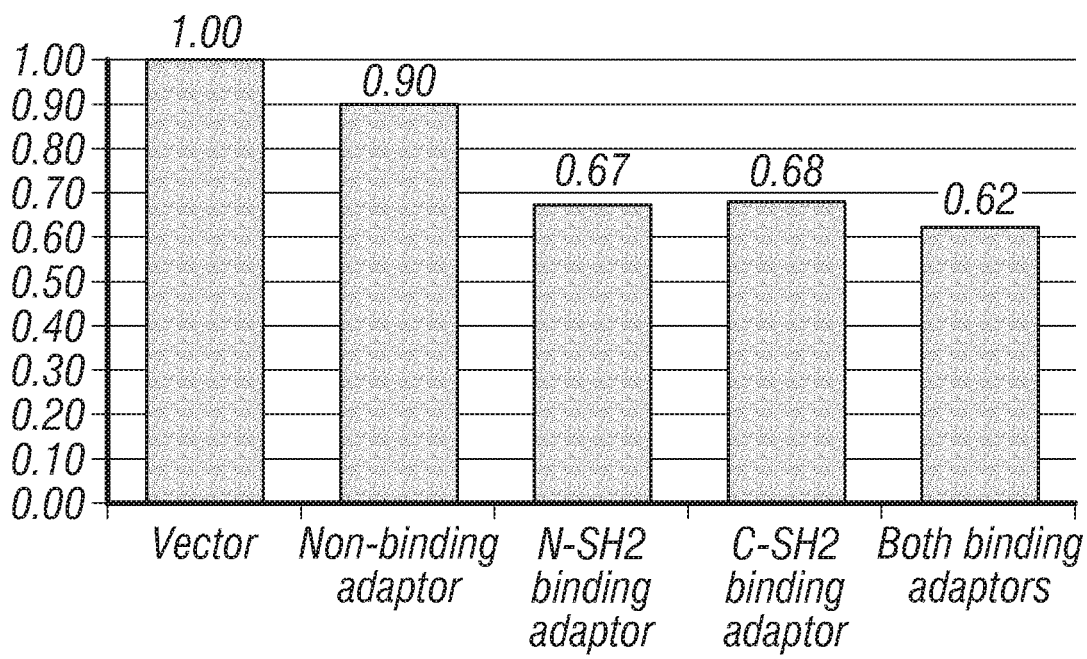

FIGS. 8A-8C: Adaptor transfection leads to endogenous Shp2 depletion in HEK293T cells. (A) Histogram overlays of GFP fluorescence (arbitrary units) of both binding and non-binding adaptors. (B) Western blot of cell lysates and (C) Image J quantification of 293T cells transfected with vector, non-binding adaptor, each binding adaptor, and both binding adaptors simultaneously.

DESCRIPTION OF ILLUSTRATIVE EMBODIMENTS

Figure 1:
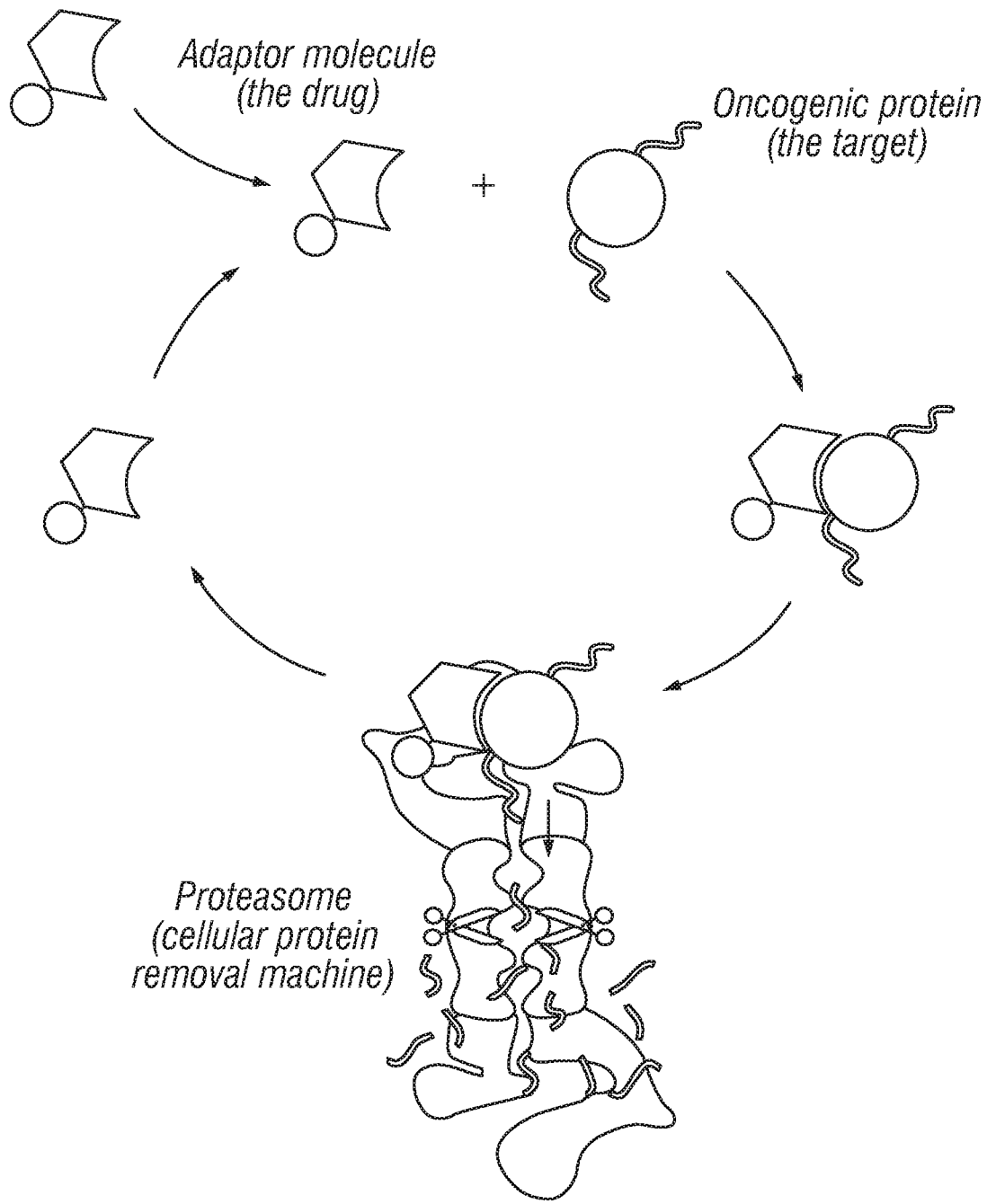
FIG. 1: Schematic of a proteasome adaptor (degradon) shunting an oncogenic protein to destruction by cellular proteasome. In this direct targeting process, a degradon molecule, composed of a proteasome-binding domain (small circle) attached to an affinity reagent binds to an oncogenic protein and shuttles the target to the proteasome for destruction. The degradon molecule is not degraded and is recycled back in the cell.

Embodiments of the present disclosure provide methods and compositions to deplete specific proteins from cells by targeting them directly to the proteasome for destruction, even without the need for ubiquitination (see, e.g., FIG. 1). The proteasome is a powerful proteolytic machine that is able to degrade nearly any protein[9,10]. The UPS can clear even large amounts of damaged proteins due to a feedback mechanism that increases proteasome synthesis when the cell senses increased demand[11-16]. Proteins are normally targeted to the proteasome by the attachment of ubiquitin tags[6,17,18]. However, ubiquitin tags are used to control other cellular events such as membrane trafficking and certain signaling cascades, and it is not fully understood how the different fates are specified[6]. Therefore, manipulation of the ubiquitination system risks pleiotropic consequences[19]. Indeed, ubiquitination is not required for degradation and is thought to act primarily as a protein-protein interaction module[20]. In the system presented here, ubiquitination is circumvented by constructing catalytic proteasome adaptor molecules that physically (non-covalently) link the target proteins to the proteasome and feed the proteins into its proteolytic core[21]. These proteasome adaptors are also referred to simply as adaptors or degradons.

In studies detailed herein, artificial proteasome adaptors, referred to as degradons, comprising a proteasome-binding domain fused to a target recognition domain were built. The proteasome-binding domain comes from the ubiquitin-like (UbL) domain in the human homologue of yeast Rad23, hHR23b. hHR23b belongs to the class of UbL-UBA proteins found in all eukaryotic organisms[27,28], which enhance the degradation of certain proteins by shuttling them to the proteasome[28]. In cells, hHR23b binds to the proteasome through an N-terminal ubiquitin-like (UbL) domain and to the target protein through a C-terminal ubiquitin-associated (UBA) domain and thus delivers the protein directly to the substrate entrance of the proteasome[30,31]. The hHR23b protein itself escapes degradation and recycles to deliver the next protein for destruction[32,33].

The degradons recognize their substrates through a target-binding domain, such as an antibody mimic called a monobody (also known as Adnectins, see reference 34-35, the contents of which are incorporated herein by reference). Monobodies resemble the antigen-binding domain of antibodies and can be evolved against a wide range of targets[36,37]. They interact with their ligands through larger interfaces than small molecules, which allows them to recognize their targets with high affinity and sufficient specificity to discriminate between members of homologous protein families[38-40]. Exemplary degradons provided herein were built around the HA4 monobody, that recognizes the Src homology 2 (SH2) domain of the tyrosine kinase Abl1, as well as an oncogenic derivative of Abl, BCR-Abl (see reference 38-39, the contents of which are incorporated herein by reference). BCR-Abl causes chronic myelogenous leukemia (CML) and is the target of the small molecule tyrosine kinase inhibitor imatinib (Gleevec)[43]. Other monobodies, called Nsa1 and Cs1 used here target the SH2 domain of Shp2 (see reference 40, the contents of which are incorporated herein by reference).

Using both in vitro and in-cell techniques, it has been demonstrated that the degradons of the embodiments efficiently promote the degradation of the target protein. Thus, the degradons provided herein can be used in a novel strategy for depleting cellular proteins, which can be applied as a research tool to study intracellular protein function and has the potential for therapeutic use.

I. DEGRADONS

As used herein the term "degradon" refers to a recombinant polypeptide comprising a target binding domain and a proteasome-binding domain (e.g., a ubiquitin-like domain). A degradon can comprise from N-terminus to C-terminus (a) the target binding domain and (b) proteasome binding domain or from N-terminus to C-terminus (a) proteasome binding domain and (b) the target binding domain. Optionally, the degradon can comprise a linker sequence positioned between the target binding domain and proteasome binding domain.

The degradon systems of the embodiments provide a method to deplete specific proteins from cells by targeting them to the proteasome for destruction through synthetic adaptor proteins called degradons. Generally, degradons comprise a recognition element to select the target protein and a carrier element (a ubiquitin-like domain) that shuttles the target to the proteasome for proteolysis. This strategy has several advantages over current methods. First, degradons act directly on the target protein, so depletion is not limited by the intrinsic turnover rates of the protein and the data suggest destruction can be rapid and substantial or even complete. Also, the ubiquitin proteasome system (UPS) is robust and designed to degrade hundreds of regulatory proteins in addition to misfolded and damaged proteins in the cytosol and nucleus of eukaryotic cells[27], and the proteasome's power can be harnessed for the purposes of this technology. In addition, degradons can be derived from natural proteasome substrate receptors and redesigned to function as specific proteasome adaptor molecules or degradons. In some aspects, degradons link the target directly to the proteasome, circumventing the ubiquitination pathway. Avoiding the ubiquitination step may allow degradons reduce off-target effects.

Further, degradons of the embodiments are versatile and customizable. They can be evolved or designed to target almost any protein and to recognize specific PTMs. The degradons tested in the examples recognize their targets by protein affinity agents derived from the tenth domain of fibronectin type III called monobodies which are easy to synthesize and contain simple sequences that can be evolved against a wide range of targets[36,37].

Finally, degradons have therapeutic potential. The degradons of the examples, for instance, contain monobodies, which in themselves are therapeutically relevant, and several are currently in phase II clinical trials[35,42]. Thus far, most monobodies act by simply blocking protein-protein interactions. This not only limits the processes that can be targeted, but also means that monobodies can only act on one target molecule at a time, thus requiring high dosages to be effective. These degradons are designed to escape proteasomal degradation[32,33,53,54], which allow them recycle and to act catalytically. This could potentially increase their power by orders of magnitude.

The degradons described in the examples bind to the proteasome through the UbL domain of Rad23 or hHR23b. Other proteasome interaction domains may be effective too. For example, HPV E7 binds to both the target protein Rb[57] and the S4 subunit of the proteasome[58] with high affinity, which allows direct proteasome targeting, bypassing the ubiquitination machinery[18,59]. The interactions of E7 with the proteasome[58] and Rb[57] have been defined and E7's proteasome binding domain could be used in degradons. Similarly, the protein gankyrin binds to Rb[60] and the proteasome subunit S6[61,62] and gankyrin's proteasome binding domain could be incorporated into degradons. Other binding modalities will also be explored in the future.

The degradons described in the examples were built using monobodies as the substrate targeting head. Other targeting strategies are feasible and in the future, degradons constructed from additional types of targeting domains will be tested. Antibodies, represent a fast growing class of drugs[41]. In most current implementations they are directed against cell surface molecules to block their action. Human antibodies offer an attractive avenue for therapeutics because they can be raised to bind tightly (low picomolar to nanomolar affinities) to many targets and have inherently low immunogenicity[63]. Smaller derivatives of antibodies, such as single chain antibodies (scFvs) and $F_{ab}$ fragments, may be more suitable for some applications, especially those where Fc-mediated effects are undesirable[64]. Two specifically designed target recognition domains will be tested. Omomyc is a Myc-binding domain derived from Myc's binding partner Max and mutated to increase the specificity and affinity of Omomyc-Myc dimer formation[65]. Generalizable computational protein design strategies have been developed to engineer protein—protein interaction surfaces[66]. Affinity reagents that recognize Mdm2 or MdmX with high affinity and specificity will also be tested. The tightest binders recognize Mdm2 with sub-nanomolar dissociation constants and discriminate between Mdm2 and MdmX by a thousand-fold[67]. Incorporating any of these affinity reagents into degradons may turn them into catalytically acting agents, greatly enhancing their power.

In the examples, degradons were delivered into cells by transfection, which is a viable delivery method for a research tool. Current protein drugs work extracellularly but several strategies have been developed to allow proteins to enter cells: the attachment of cell-penetrating peptides[68-70], receptor-mediated delivery systems[71], and mRNA delivery[72,73]. In the future, all three delivery strategies will be tested on degradons. Gene therapy, the delivery of genes to somatic cells in animals, is making significant progress[74,75] and may eventually become a feasible delivery approach for degradons.

Thus, embodiments detailed herein provide system has been developed that specifically targets and destroys the Abl or the Shp2 SH2 domain by using adaptors, or degradons, to shuttle it to the proteasome. Using both in vitro and in-cell techniques, it has been demonstrated that these degradons efficiently promote the degradation of our target proteins. The system has also been used to destroy Shp2 protein in cells. Together, these results describe a novel strategy for depleting cellular proteins, which can be applied as a research tool to study intracellular protein function and has the potential for therapeutic use.

II. TARGET BINDING DOMAINS

Targeting domains for use in degradons of the embodiments can include antibodies or fragments thereof, such as monoclonal antibodies, single chain antibodies (scFvs), Fv fragments or Fab fragments. Monoclonal antibodies to a target molecule can be made using standard methods such as, for example, hybridoma-based methods, genetically altered and transgenic mouse-based methods, recombinant methods, and display methods. Human antibodies can be made using methods such as, for example, transgenic mice comprising human heavy chain and light chain loci, human B-lymphocytes, recombinant methods, and display methods. In certain embodiments, monoclonal antibodies may be manipulated by recombinant techniques. In certain such embodiments, nucleic acid(s) encoding the heavy chain and light chain of the monoclonal antibody chains may be isolated and cloned from the cell expressing the antibody. For example, RNA can be prepared from cells expressing the desired antibody, such as mature B-cells or hybridoma cells, using standard methods. The RNA can then be used to make cDNA using standard methods, and the cDNA can be amplified, for example, by PCR, using specific oligonucleotide primers.

In certain embodiments, human or non-human antibodies are chimerized. In certain embodiments, mouse monoclonal antibodies are chimerized by replacing the mouse Fc with a human Fc. In certain embodiments, human monoclonal antibodies are chimerized by replacing the human Fc with a non-human animal Fc. In certain embodiments, the human Fc is replaced with a mouse Fc. Certain exemplary methods for making chimeric antibodies are provided, for example, in Morrison et al. (1984) Proc. Nat'l Acad. Sci. USA 81:6851-6855; Neuberger et al. (1984) Nature 312:604-608; Takeda et al. (1985) Nature 314:452-454; and U.S. Pat. Nos. 6,075,181 and 5,877,397.

In certain embodiments, non-human antibodies are "humanized." As a non-limiting example, a mouse monoclonal antibody that specifically binds the target molecule may be humanized in order to reduce immunogenicity (e.g., reduced human anti-mouse antibody (HAMA) response) when administered to a human. In certain embodiments, a humanized antibody has a similar binding affinity for the target molecule as the non-humanized parent antibody. In certain embodiments, a humanized antibody has increased binding affinity for the target molecule when compared to the non-humanized parent antibody. Certain exemplary humanization methods include, but are not limited to, CDR grafting and human engineering, as described in detail below.

In certain embodiments, one or more complementarity determining regions (CDRs) from the light chain and/or heavy chain variable regions of an antibody with the desired binding specificity (the "donor" antibody) are grafted onto human framework regions (FRs) of the light and/or heavy chain of an "acceptor" antibody in order to create a humanized antibody with the binding specificity of the donor antibody.

In certain embodiments, cDNA encoding a heavy chain and/or light chain can be modified in order to modify the expressed heavy and/or light chain. For example, in certain embodiments, the constant region of a mouse heavy or light chain can be replaced with the constant region of a human heavy or light chain. In this manner, in certain embodiments, a chimeric antibody can be produced which possesses human antibody constant regions but retains the binding specificity of a mouse antibody. Alternatively, the constant region of a human heavy or light chain can be replaced with the constant region of a non-human animal heavy or light chain. In this case, a chimeric antibody can be produced which possesses non-human animal antibody constant regions, e.g., for expression in a non-human animal model, but retains the binding specificity of the human antibody.

III. TARGET PROTEINS

Degradon targets can include proteins that are involved in a disease. For example, they include mutant proteins, such a proteins encoded by genes that are inherited. In further aspects, the target proteins are encoded by oncogenes such as BCL2, c-MYC, Ras and HER2. Other exemplary oncogenes included, but are not limited to, BCR/ABL, ABL1/BCR, ABL, BCL1, CD24, CDK4, EGFR/ERBB-1, HSTF1, INT1/WNT1, INT2, MDM2, MET, MYB, MYC, MYCN, MYCL1, RAF1, NRAS, REL, AKT2, APC, BCL2-ALPHA, BCL2-BETA, BCL3, BCR, BRCA1, BRCA2, CBL, CCND1, CDKN1A, CDKN1C, CDKN2A, CDKN2B, CRK, CRK-II, CSF1R/FMS, DBL, DDOST, DCC, DPC4/SMAD4, E-CAD, E2F1/RBAP, ELK1, ELK3, EPH, EPHA1, E2F1, EPHA3, ERG, ETS1, ETS2, FER, FGR, FLI1/ERGB2, FOS, FPS/FES, FRA1, FRA2, FYN, HCK, HEK, HER3/ERBB-2, ERBB-3, HER4/ERBB-4, HST2, INK4A, INK4B, JUN, JUNB, JUND, KIP2, KIT, KRAS2A, KRAS2B, LCK, LYN, MAS, MAX, MCC, MLH1, MOS, MSH2, MYBA, MYBB, NF1, NF2, P53, PDGFB, PIM1, PTC, RB1, RET, ROS1, SKI, SRC1, TAL1, TGFBR2, THRA1, THRB, TIAM1, TRK, VAV, VHL, WAF1, WNT2, WT1, YES1, ALK/NPM1, AMI1, AXL, FMS, GIP, GLI, GSP, HOX11, HST, IL3, INT2, KS3, K-SAM, LBC, LMO-1, LMO-2, L-MYC, LYL1, LYT-10, MDM-2, MLH1, MLL, MLM, N-MYC, OST, PAX-5, PMS-1, PMS-2, PRAD-1, RAF, RHOM-1, RHOM-2, SIS, TAL2, TAN1, TIAM1, TSC2, TRK, TSC1, STK11, PTCH, MEN1, MEN2, P57/KIP2, PTEN, HPC1, ATM, XPA/XPG, BCL6, DEK, AKAP13, CDH1, BLM, EWSR1/FLI1, FES, FGF3, FGF4, FGF6, FANCA, FLI1/ERGB2, FOSL1, FOSL2, GLI, HRAS1, HRX/MLLT1, HRX/MLLT2, KRAS2, MADH4, MAS1, MCF2, MLLT1/MLL, MLLT2/HRX, MTG8/RUNX1, MYCLK1, MYH11/CBFB, NFKB2, NOTCH1, NPM1/ALK, NRG/REL, NTRK1, PBX1/TCF3, PML/RARA, PRCA1, RUNX1, RUNX1/CBFA2T1, SET, SHP2, TCF3/PBX1, TGFB1, TLX1, P53, WNT1, WNT2, WT1, αv-β3, PKCα, TNFα, Clusterin, Survivin, TGFβ, c-fos, c-SRC, and INT-1.

IV. CELL PENETRATING PEPTIDES

Furthermore, in certain aspects, degradons can include segments of sequence that encode a cell penetrating peptide (CPP) As used herein the terms "cell penetrating peptide" refers to segments of polypeptide sequence that allow a polypeptide to cross the cell membrane (e.g., the plasma membrane in the case a eukaryotic cell). Examples of CPP segments include, but are not limited to, segments derived from HIV Tat (e.g., GRKKRRQRRRPPQ (SEQ ID NO: 16)), herpes virus VP22, the *Drosophila* Antennapedia homeobox gene product, protegrin I, Penetratin (RQIKIWFQNRRMKWKK (SEQ ID NO: 17)) or melittin (GIGAVLKVLTTGLPALISWIKRKRQQ (SEQ ID NO: 18)). In certain aspects the CPP comprises the T1 (TK-IESLKEHG (SEQ ID NO: 19)), T2 (TQIENLKEKG (SEQ ID NO: 20)), 26 (AALEALAEALEALAEALEA-LAEAAAA (SEQ ID NO: 21)) or INF7 (GLFEAIEGFIEN-GWEGMIEGWYGCG (SEQ ID NO: 22)) CPP sequence.

V. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1-Construction of Degradons and Target Proteins

To test whether degradons are able to induce the degradation of proteins by the proteasome, a reliable readout to easily measure target protein abundance was needed. The target proteins, Abl and Shp2 SH2 domains, were attached to green fluorescent protein (GFP) both because its intrinsic protein fluorescence is directly proportional to the concentration of GFP, and because it has been used extensively in vitro and in vivo[47,48]. In addition, because GFP has a long halftime in vitro and in vivo and is challenging for the proteasome to degrade[49,50], successfully degrading GFP should demonstrate the system's robustness. Therefore, for the target protein, the SH2 domain of human c-Abl and either the N-terminal or C-terminal SH2 domain of Shp2 was fused to the N-terminus of GFP. A 35 amino acid long disordered sequence was added to the C-terminus of GFP to create the final substrate protein SH2-GFP-tail (FIG. 2, bottom). The tail was included to represent the unstructured regions often found in regulatory proteins and to provide a region at which the proteasome can initiate degradation[51,52]. Many regulatory proteins, including Abl and BCR-Abl, and Shp2 contain unstructured regions that can serve as proteasome initiation sites.

To target the model protein for degradation in vitro, a set of degradons was constructed consisting of a monobody (mB) domain attached through a flexible linker to the UbL domain of *S. cerevisiae* Rad23 (FIG. 2). The monobody domain, HA4, Nsa1, and Cs1, was previously described (see, e.g., references 38-40, incorporated herein by reference) and binds the SH2 domain of Abl and BCR-Abl or Shp2 with nanomolar affinities. The degradons bind to the proteasome through the UbL domain of Rad23[32,33,53]. The flexible linker is also derived from Rad23 and has evolved to escape recognition by the proteasome due to its length and amino acid sequence, increasing the stability and catalytic function of the degradons[33,54]. Two different lengths of linker and two different geometries: an N-terminal UbL domain followed by a linker and then a C-terminal monobody or an N-terminal monobody domain followed by linker and a C-terminal UbL domain were used. The resulting twelve different degradons (UbL-mB, UbL-L1-mB, mB-UbL, and mB-L1-UbL for all three SH2 domains) are shown in FIG. 2. Degradons were constructed by Gibson assembly from synthesized DNA oligos[55]. Degradons and substrates were purified from *E. coli* by affinity chromatography, and the proteasome from *S. cerevisiae*, also by affinity chromatography as described previously[56]. For the in-cell experiments, the UbL domain was derived from the human homolog of Rad23, hHR23b. A non-binding mutant (HA4 Y87A)[36] was created as a control in cells.

Example 2—Characterization of Protein Degradation System

In Vitro Degradation of Proteins is Induced by Degradons.

Figure 3B:
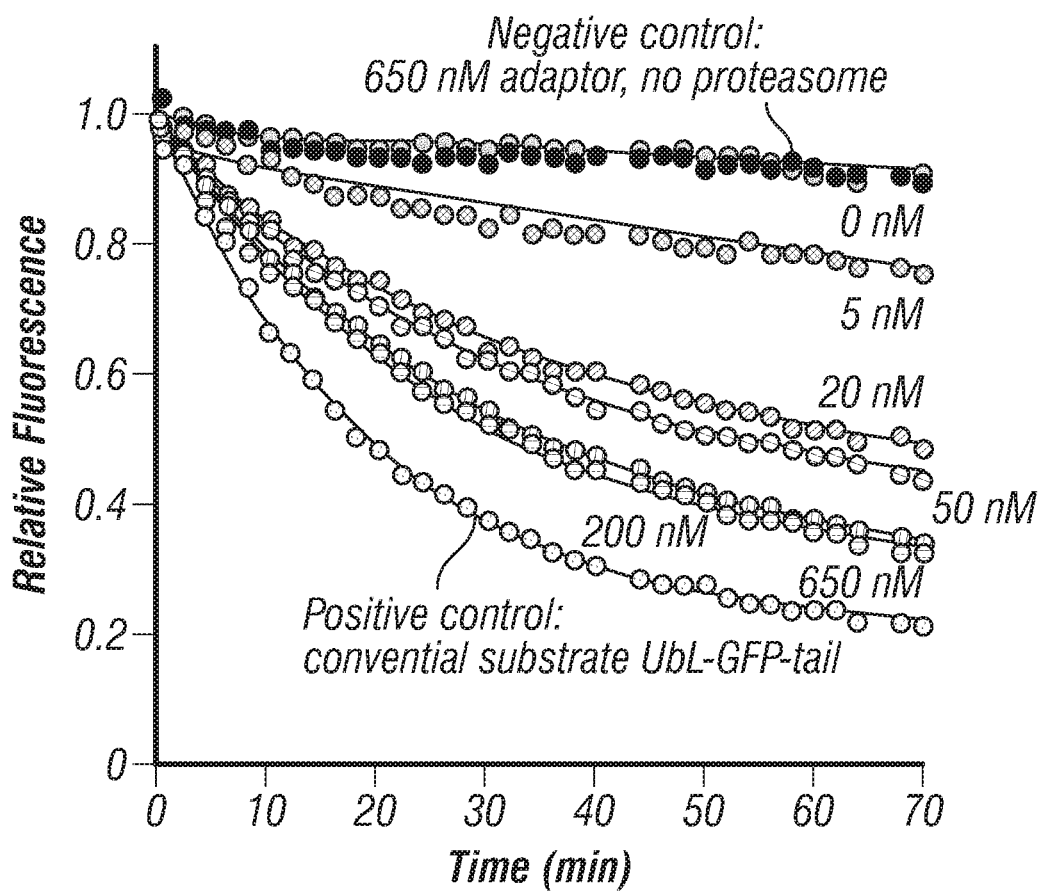
Figure 3C:
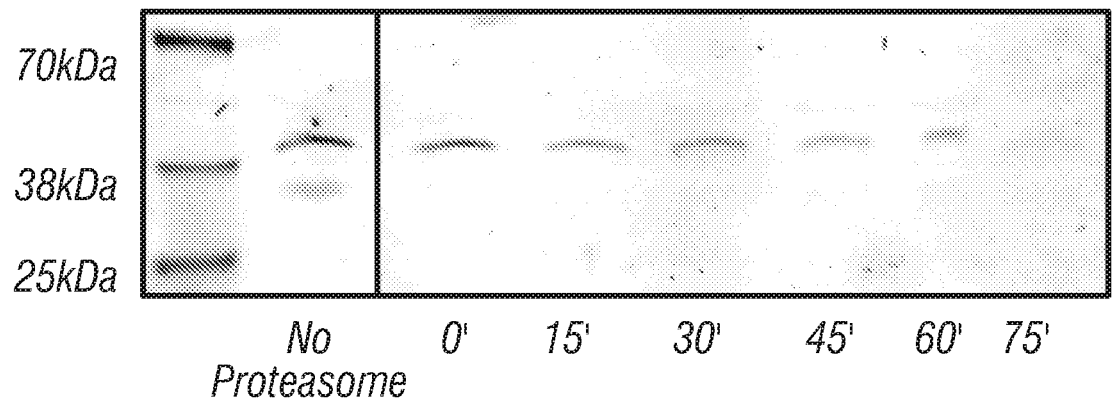
Figure 3C:
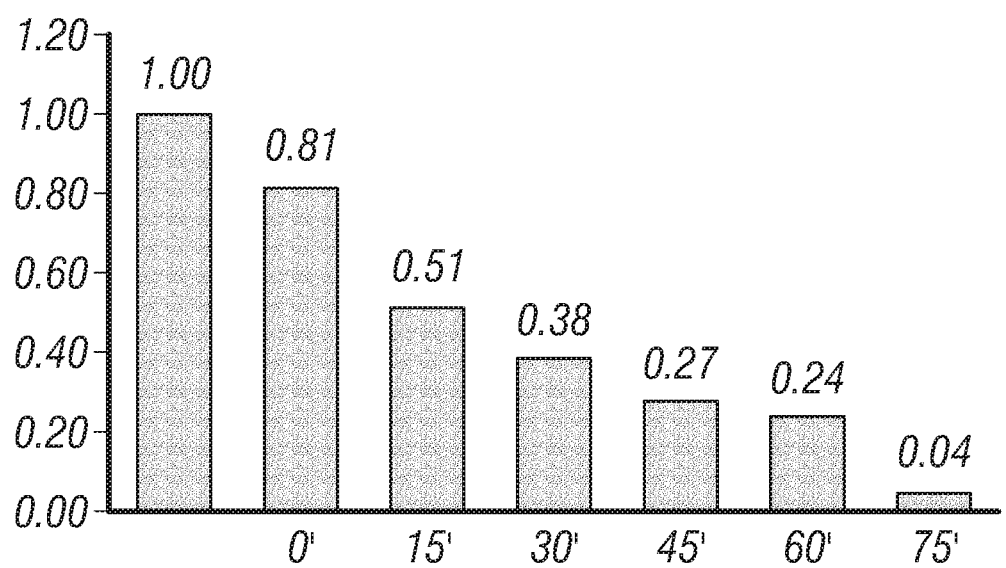
Figure 4A:
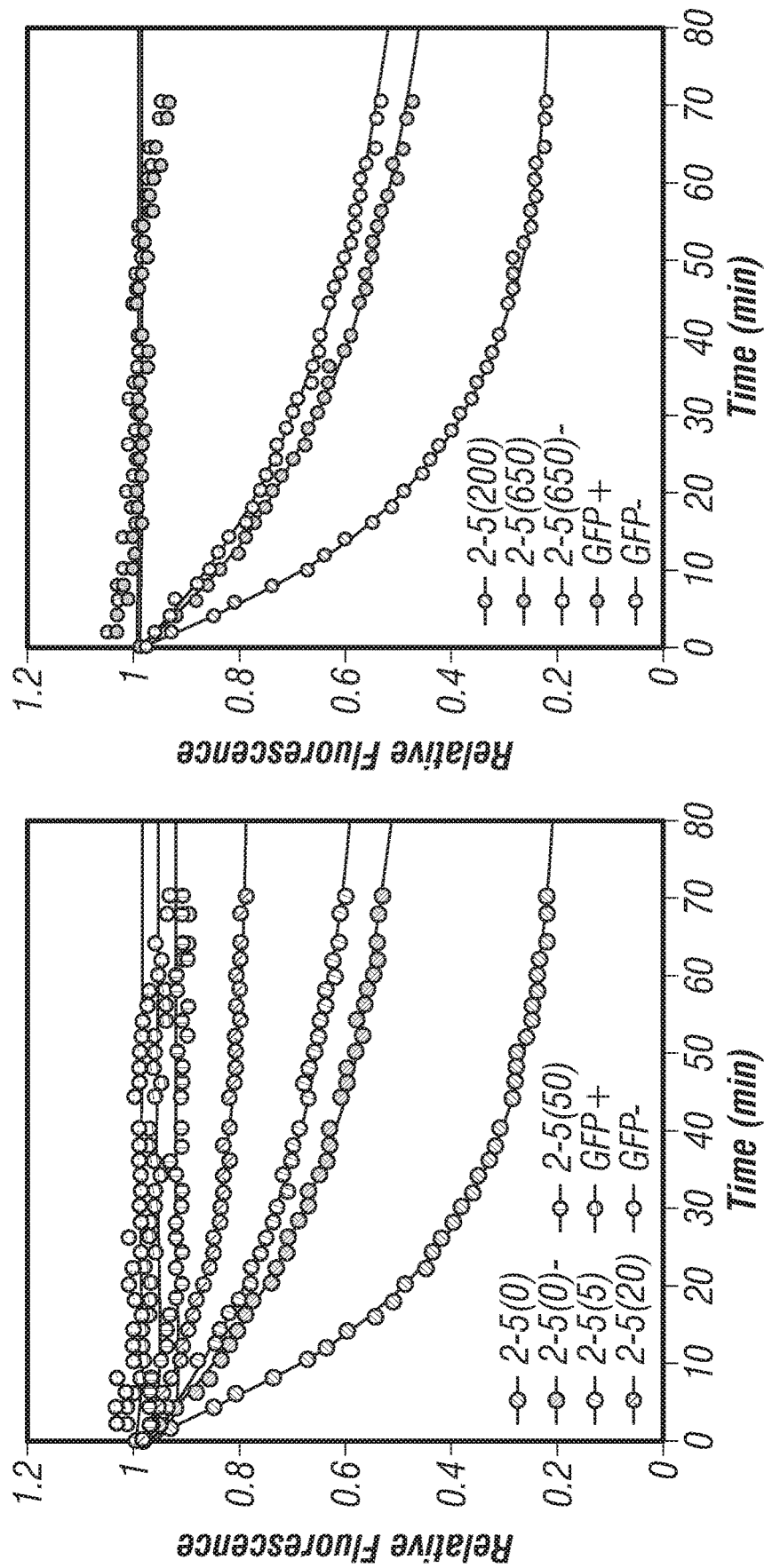
FIGS. 4A-4C: Degradation of SH2-GFP-tail by different degradon proteins. (A) mB$^{HA4}$-UbL, the GFP-control has almost no degradation, followed by 2-5(0), 2-5(0)−, 2-5(5), 2-5(20), 2-5(50), and GFP+ with the most degradation; (B) UbL-L1-mB$^{HA4}$; (C) mB$^{HA4}$-L1-UbL.
Figure 4B:
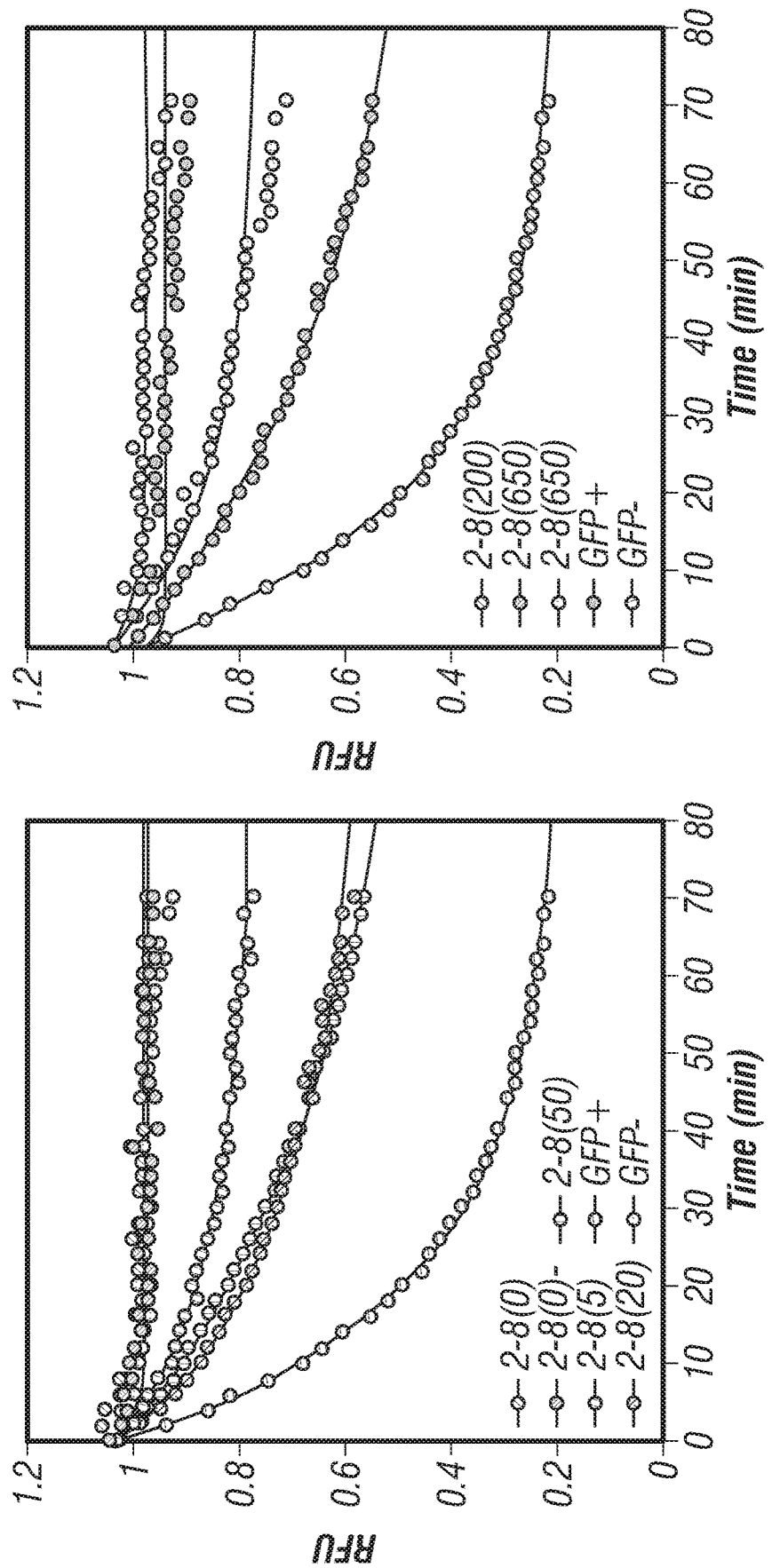
Figure 4C:
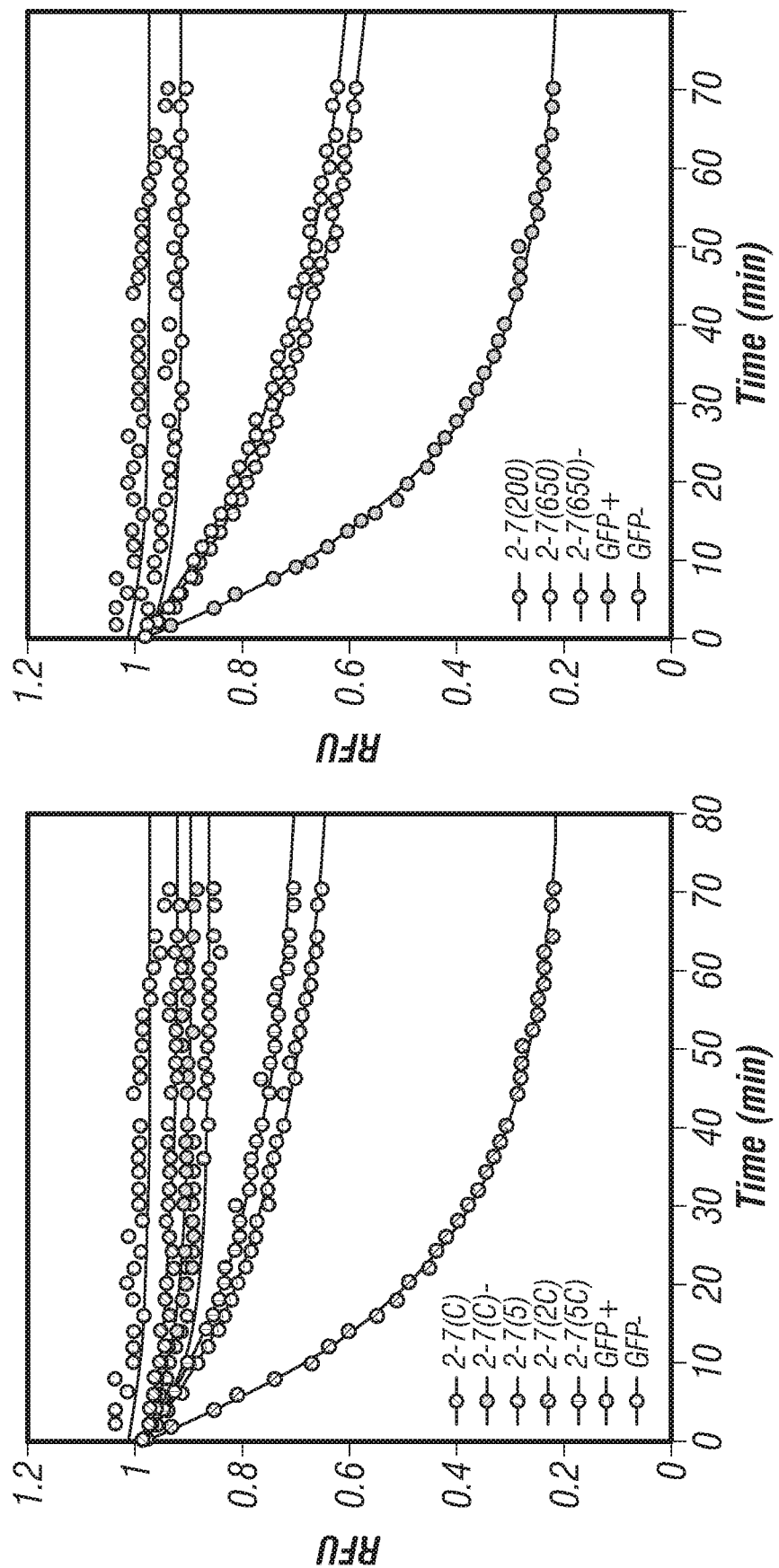

The degradation of substrate protein (FIG. 3A) was assayed in vitro by incubating it with purified yeast proteasome and a degradon in the presence of ATP and monitoring the intrinsic GFP fluorescence. As a positive control, GFP was included that contains both a UbL domain fused to its N terminus and a disordered region fused to its C terminus, which is rapidly degraded by purified yeast proteasome in the presence of ATP as shown by the exponential decrease in GFP fluorescence (FIG. 3B; positive control). Without degradon, the substrate protein remained stable, presumably because it could not bind to the proteasome in the absence of the degradon (FIG. 3B; 0 nM). However, addition of increasing amounts of the degradon (UbL-mB$^{HA4}$) led to dose-dependent degradation of the SH2-GFP-tail substrate protein (FIG. 3B; 5 nM, 20 nM, 50 nM, 200 nM, 650 nM). Degradation improved with higher concentrations of degradon but eventually leveled out, presumably because free degradon molecules began to compete with degradon-substrate complex for proteasome binding. Degradation was proteasome-dependent because leaving out the proteasome in the reaction stabilized the substrate protein to the same extent as in the absence of degradon (FIG. 3; negative control: 650 nM degradon, no proteasome). Analyzing an equivalent reaction by SDS-PAGE and quantitative fluorescent imaging (Typhoon) showed a parallel decrease in target protein (FIG. 3C). Degradation of the target protein was complete because no protein fragments were detected at the final time point (FIG. 3C). The other degradons constructed also induced degradation of SH2-GFP-tail substrate, though somewhat less effectively (FIG. 4), possibly because simultaneous degradon binding of the proteasome and substrate were length- and geometry-dependent.

The Degradons can Act Catalytically.

Figure 5:
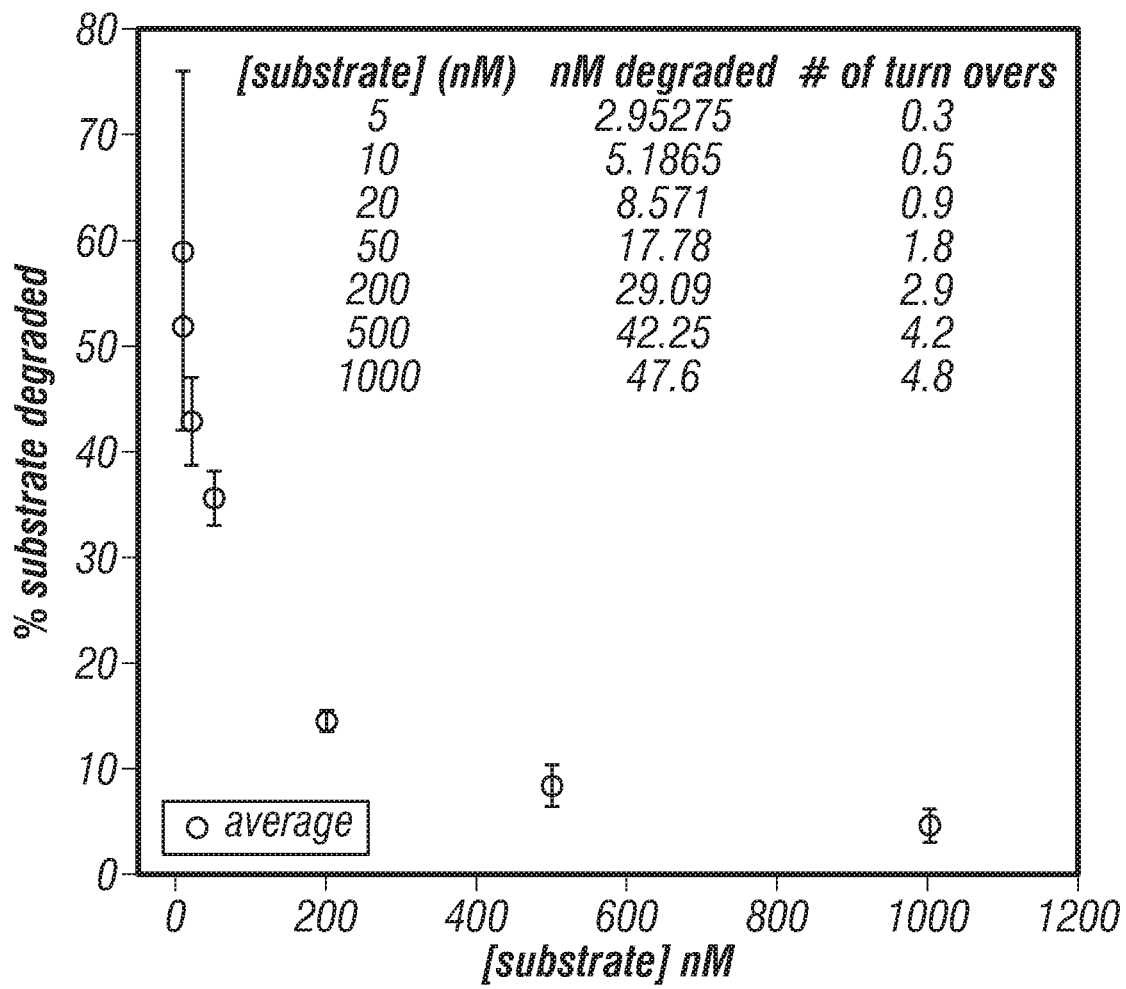
FIG. 5: Degradons can act catalytically. The indicated amounts of substrate (SH2-GFP-tail) were incubated with 10 nM degradon (UbL-mB$^{HA4}$) and proteasome in the presence of ATP. Degradation was followed by monitoring GFP fluorescence and the extent of degradation was calculated from the observed fluorescent change as a fraction of the total fluorescence.

Next, it was tested whether degradons can act catalytically, where one degradon molecule induces the degradation of several target proteins. To do so, the depletion of different concentrations of the target protein by a fixed concentration of degradon (10 nM) was assayed and the amount of degraded substrate was quantified (FIG. 5). The results showed that the degradon molecules can turn over substrates nearly five times.

Degradon Transfection Leads to Substrate Degradation in Cells.

Figure 6A:
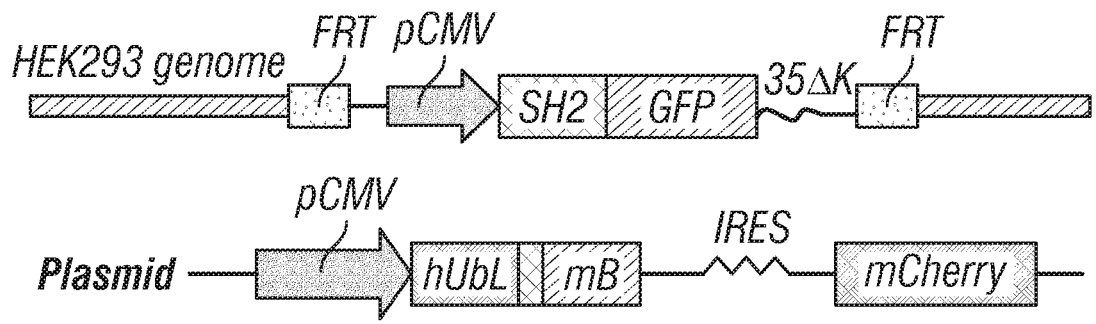
Figure 6F:
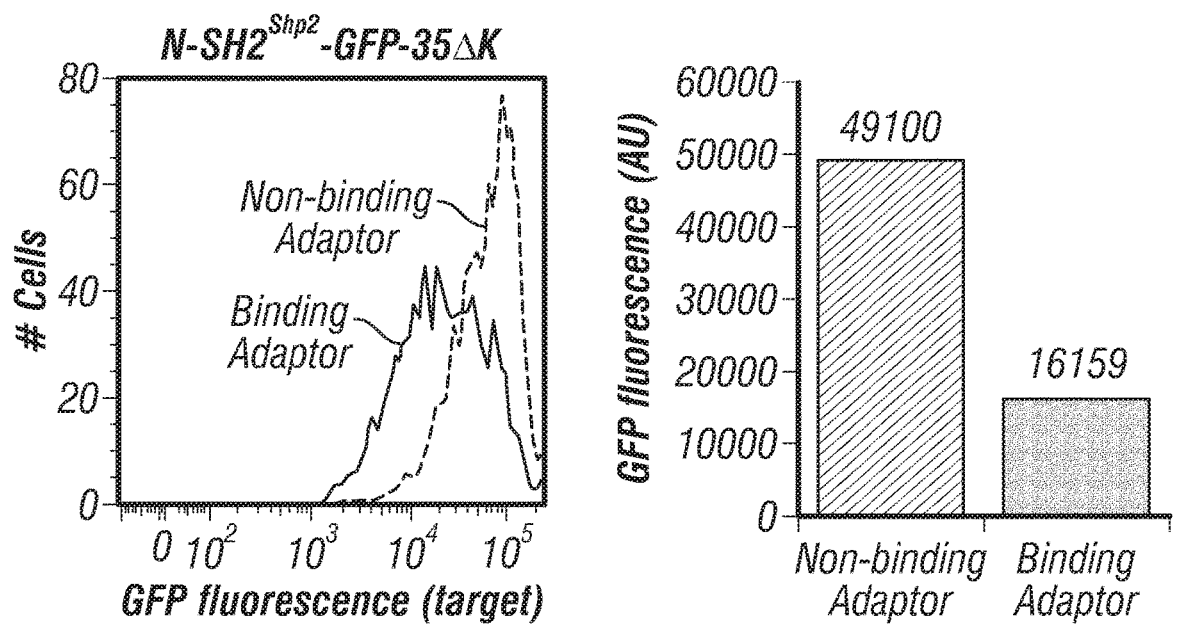
Figure 6G:
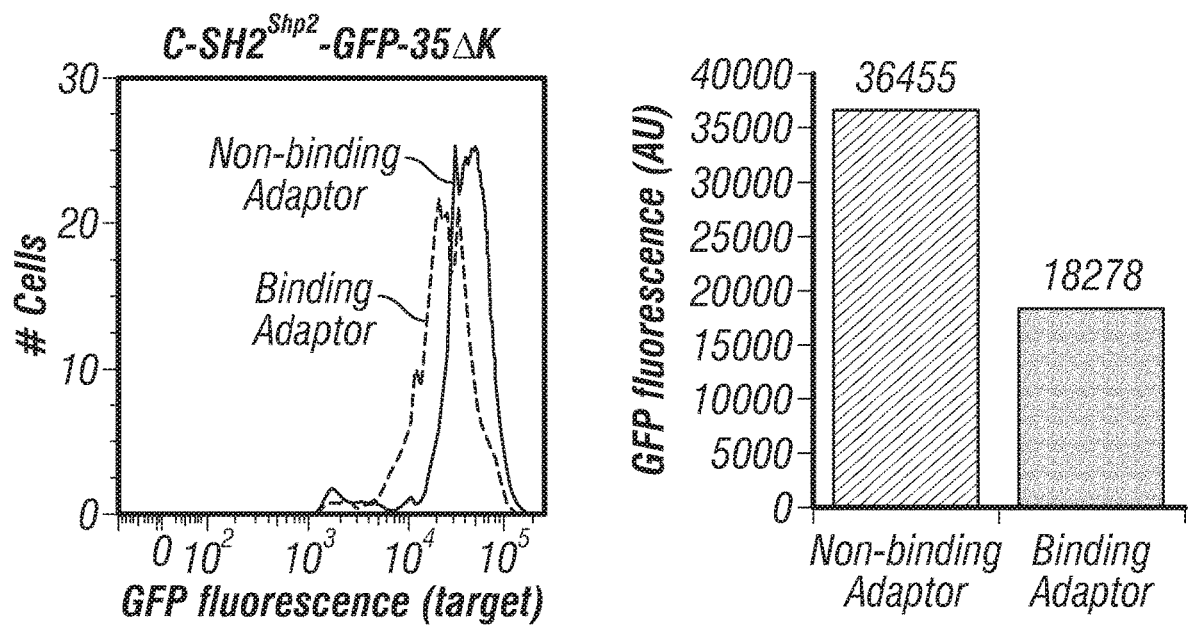
Figure 7A:
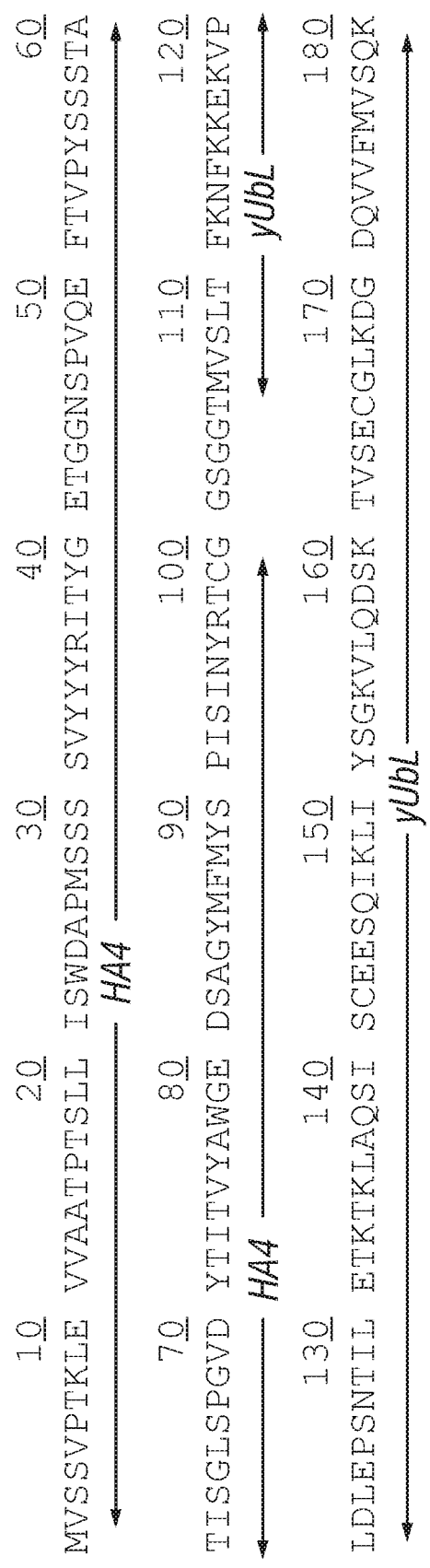
FIGS. 7A-7O: Schematics show exemplary degradon sequences of the embodiments. (7A=SEQ ID NO: 1; 7B=SEQ ID NO: 2; 7C=SEQ ID NO: 3; 7D=SEQ ID NO: 4; 7E=SEQ ID NO: 5; 7G=SEQ ID NO: 6; 7H=SEQ ID NO: 8; 7I=SEQ ID NO: 9; 7J=SEQ ID NO: 10; 7K=SEQ ID NO.
Figure 7B:
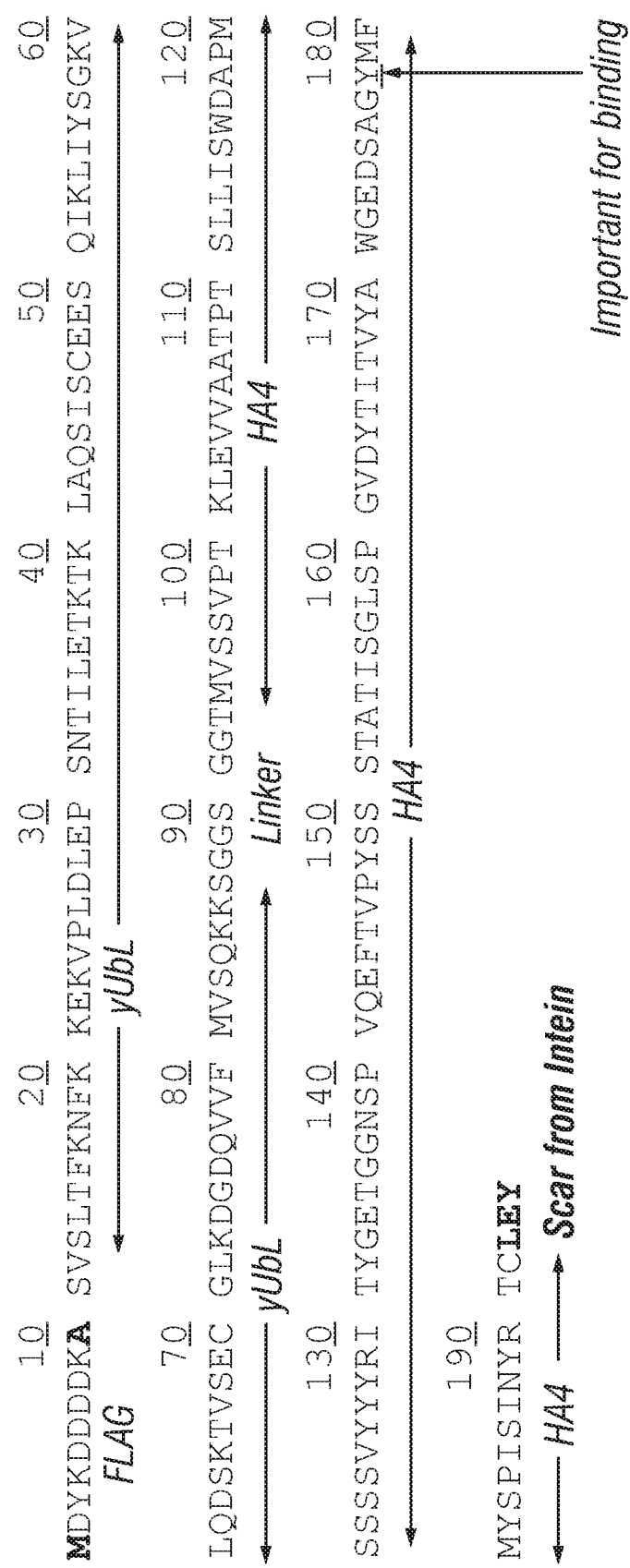
Figure 7C:
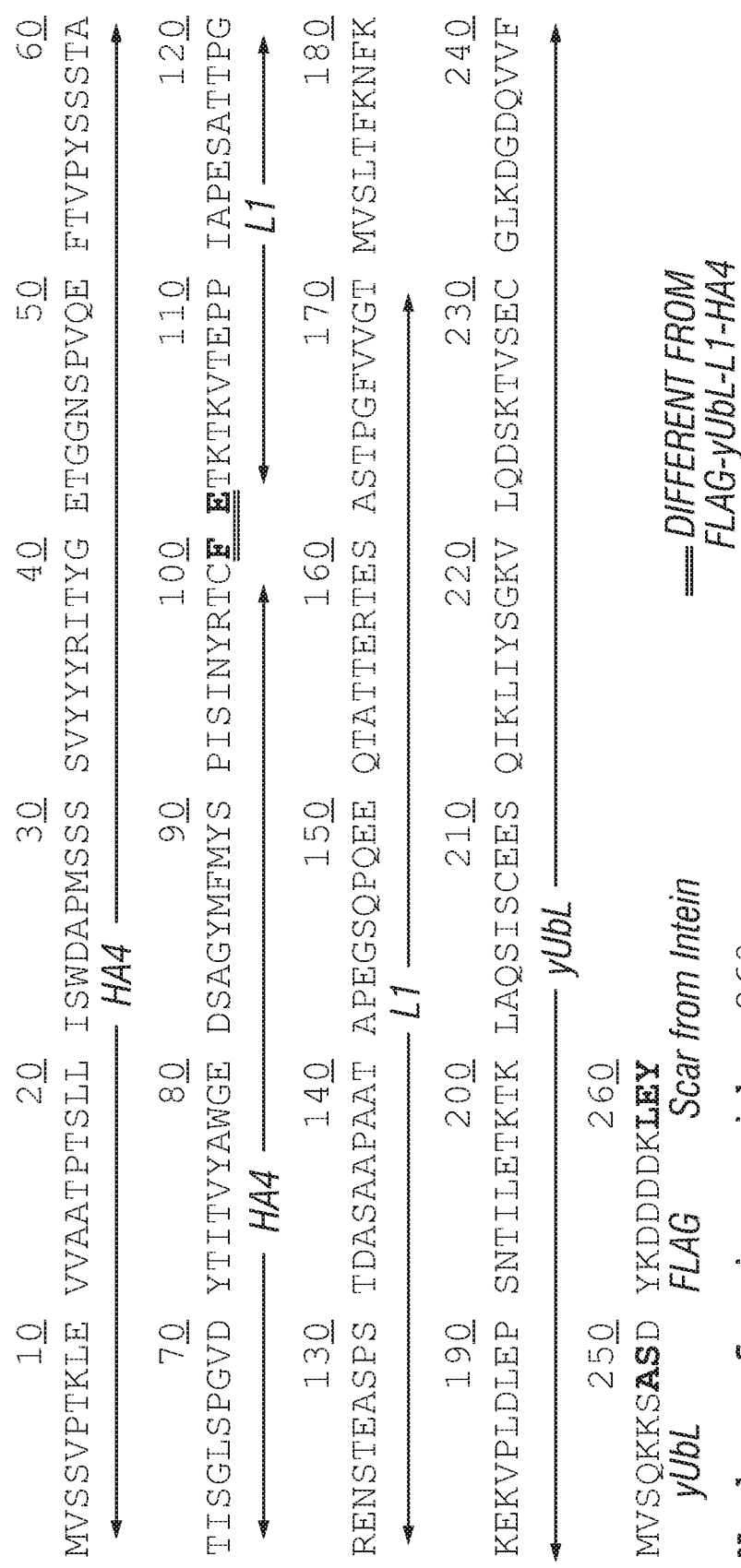
Figure 7D:
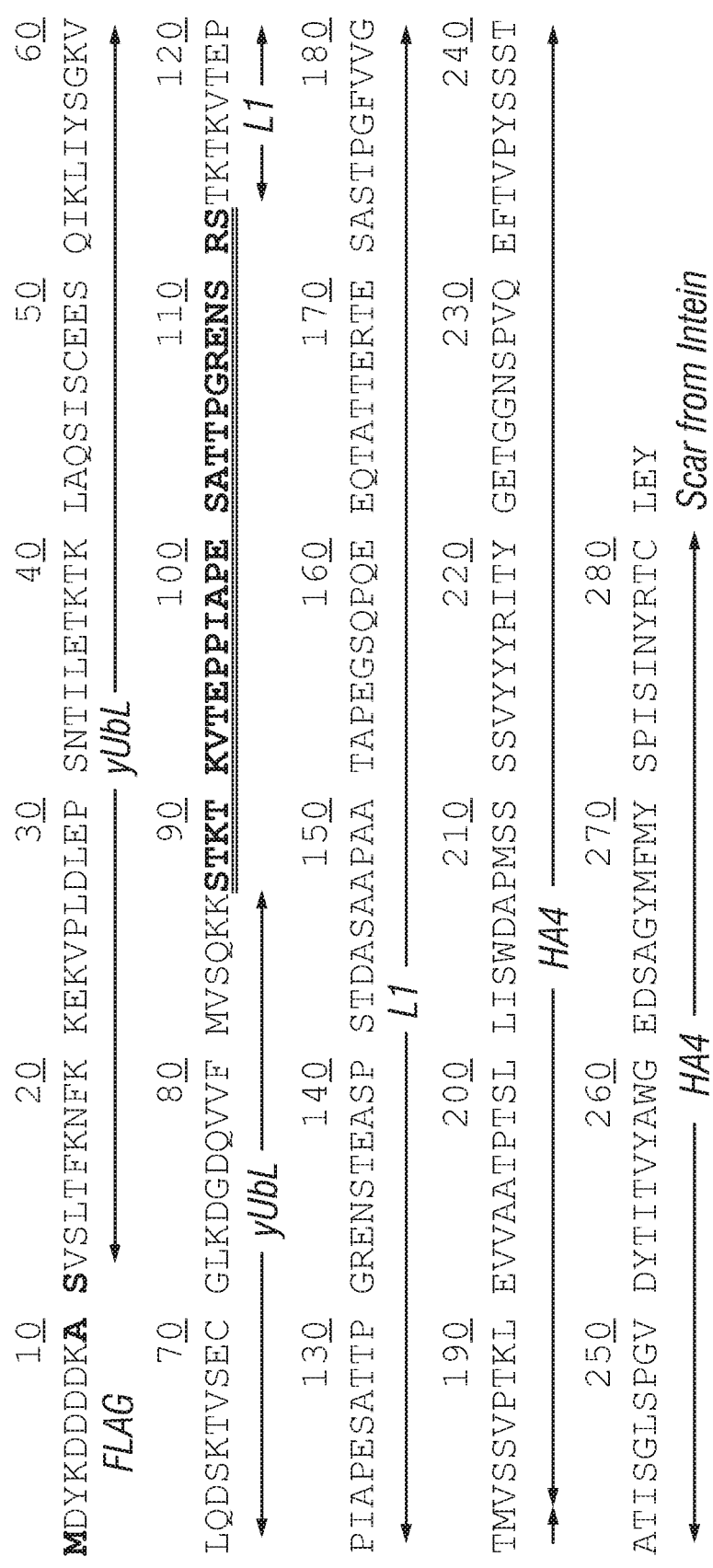
Figure 7E:
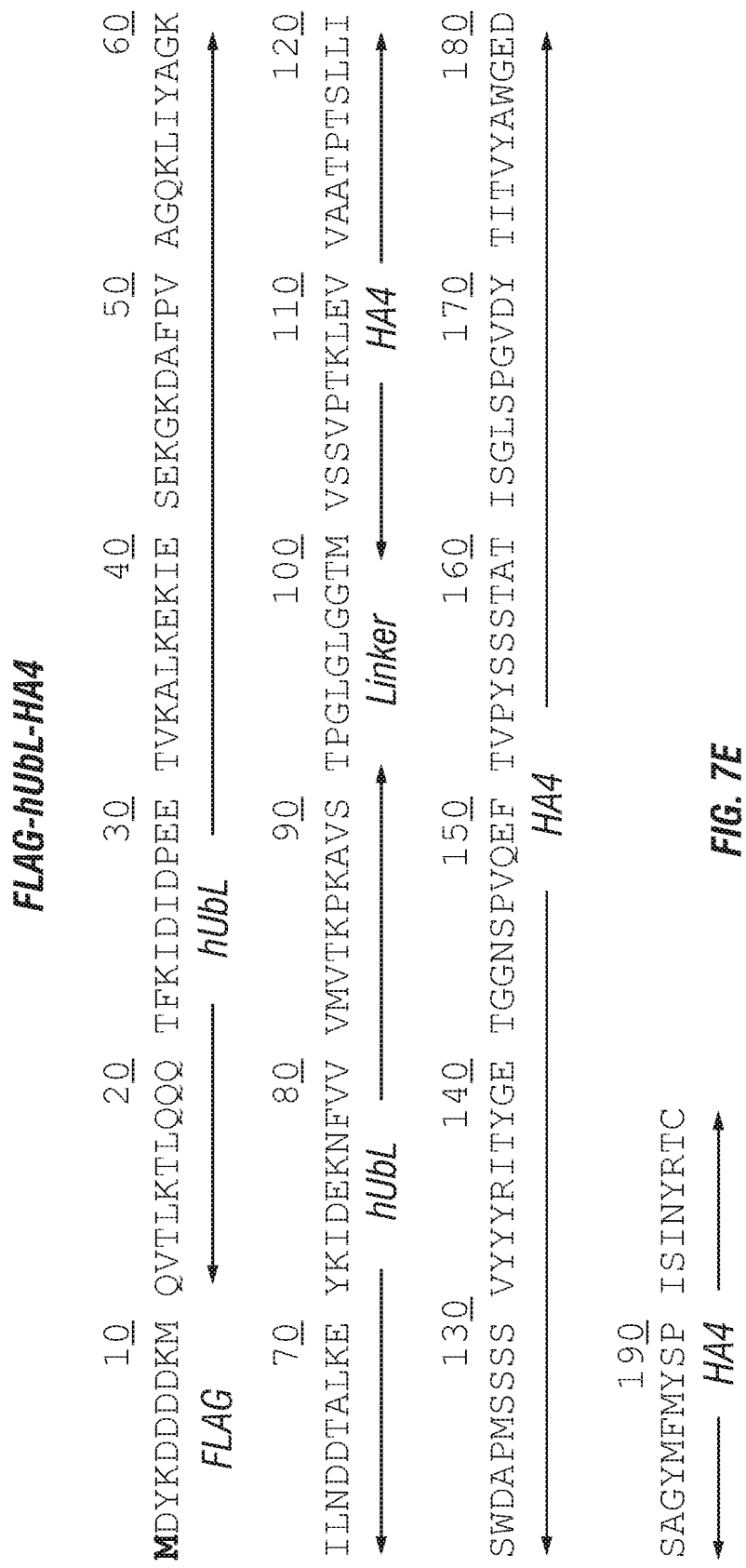
Figure 7G:
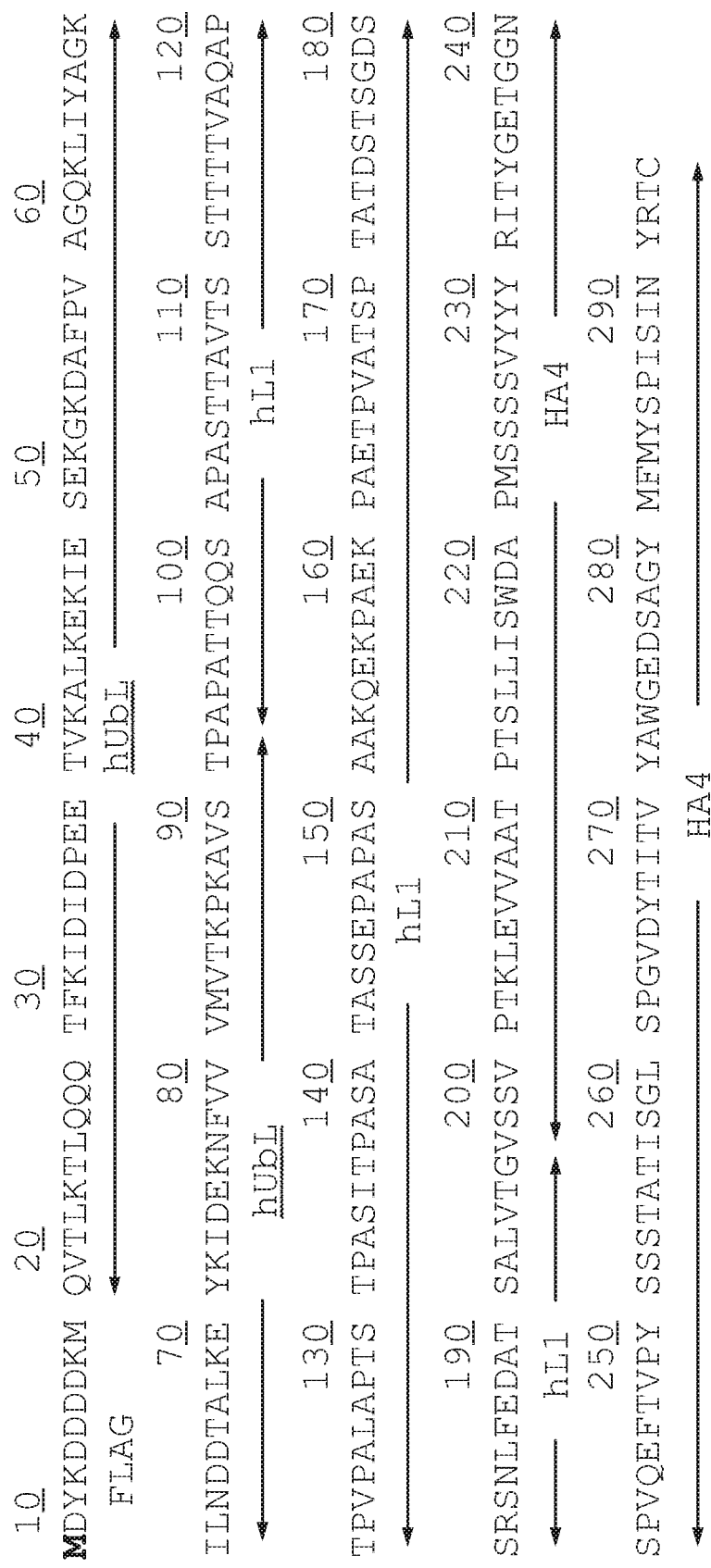
Figure 7I:
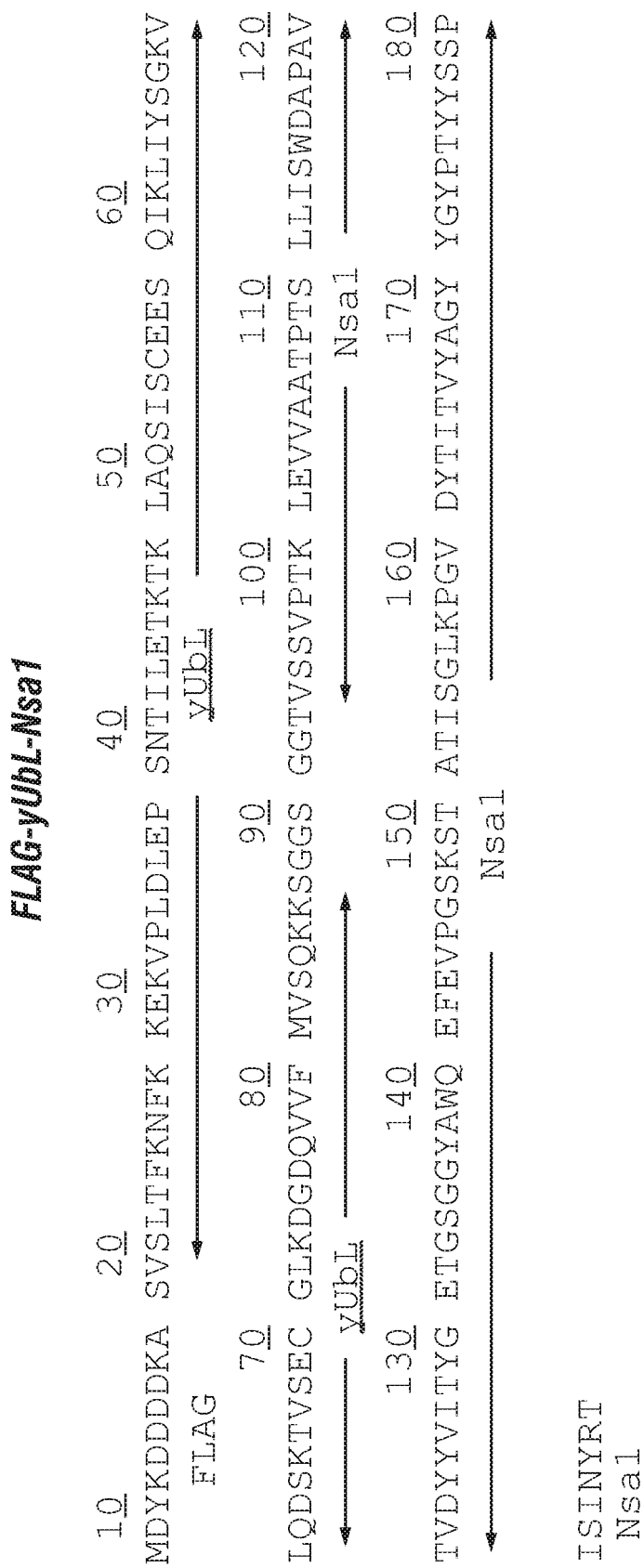
Figure 7N:
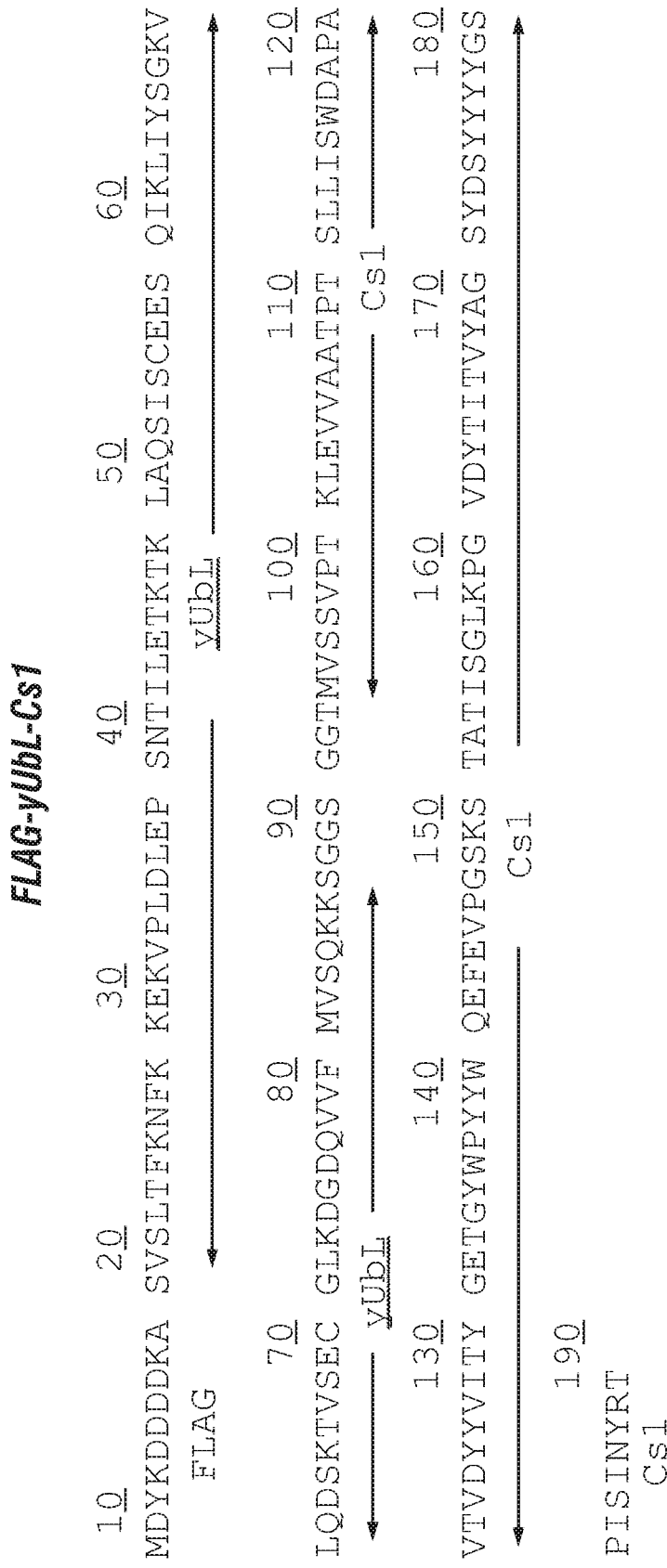

Next, an experiment was performed to determine whether the system developed in vitro could be applied to cells. First, stable HEK293 FlpIn™ cells expressing the three substrates (SH2$^{Abl}$-GFP-35ΔK, N-SH2$^{Shp2}$-GFP-35ΔK, and C-SH2$^{Shp2}$-GFP-35ΔK) through genomic integration were set up (FIG. 6A). Then, both substrate-integrated cells and host cells (no integration) were transfected with the best-degrading degradon in vitro. This degradon contained a FLAG tag fused to the UbL domain from human Rad23b, which was linked N-terminally to the monobody HA4, Nsa1, or Cs1 (FLAG-hUbL-mB$^{HA4}$, or binding adaptor or degradon). A non-binding degradon was created as a control, in which Tyr87 of HA4 was mutated to Ala (FLAG-hUbL-mB$^{HA4(Y87A)}$, or non-binding adaptor or degradon)[3]. This non-binding degradon was used as a negative control for both Abl and Shp2 experiments. In order to monitor the degradon expression levels and transfection efficiency, a C-terminal Internal Ribosome Entry Site (IRES) followed by mCherry was added (FIG. 6A). Upon transfection of binding degradon, there was a two- to four-fold decrease in substrate amount (measured as GFP fluorescence) compared to the non-binding control using Fluorescence Activated Cell Sorting (FACS) analysis (FIGS. 6B-D). In a parallel assay, cell lysate was separated on an SDS-PAGE gel and total substrate amount was measured using a Typhoon fluorescent imager (FIG. 6E, top). ImageJ quantification confirmed that the substrate was degraded four-fold only when in the presence of binding degradon (FIG. 6E, bottom). These results clearly demonstrated that the system is indeed applicable in mammalian cells.

Adaptor Transfection Leads to Endogenous Shp2 Depletion in Cells.

The next step was to determine whether the degradons were able to degrade full-length, endogenous substrate in cells. The Shp2 degradons were used to deplete endogenous Shp2, which is readily detectable in 293T cells (FIG. 8B). Each Shp2 degradon was transfected (UbL-mB$^{Nsa1}$ or UbL-mB$^{Cs1}$) and both simultaneously (in a 1:1 DNA ratio) as well as non-binding degradon (UbL-mB$^{HA4(Y87A)}$) into 293T cells. After fixing and permeabilizing the cells, they were stained with anti-Shp2 (Santa Cruz) and Alexa488-conjugated secondary antibody (Invitrogen). FACS analysis showed that endogenous Shp2 was depleted by 37% (FIG. 8A), and Western blot analysis followed by ImageJ quantification confirmed this finding (FIGS. 8B and C). These results show that the degradons can be used to deplete full-length, endogenous proteins in cells.

Example 3—Materials and Methods

Substrate and Degradon Plasmid Design.

In vitro substrates and degradons were created using Gibson Assembly PCR. Constructs were cloned into the second multiple cloning site in a pETDUET vector with a C-terminal Chitin binding domain tag followed by a 6× Histidine tag and expressed from the T7 promoter in *E. coli* strains BL21(DE3)pLysS or Rosetta(DE3)pLysS (Novagen).

The target protein consisted of the SH2 domain of Abl1 (amino acids 112-232 of human Abl1), the N-terminal SH2 domain of Shp2 (amino acids 2-103), or the C-terminal SH2 domain of Shp2 (amino acids 112-217 of human Shp2) followed by a 6 amino acid long Gly-Gly-Ser-Gly-Ser linker, the entire sequence of monomeric superfolder GFP, and finally a C-terminal 35 amino acid long sequence corresponding to amino acids 2 to 36 of yeast cytochrome b2 with all lysine residues mutated to arginine (called 35ΔK).

The proteasome adaptors (degradons) consisted of the UbL domains of yeast Rad23 (amino acids 1-77 of Rad23) for the in vitro experiments or of human Rad23b (amino acids 1-83 of Rad23b) for the cell culture experiments fused to full length HA4, Nsa1, or Cs1 monobodies[38]. In the constructs with the longer linkers an additional 69 amino acids from Rad23 following the UbL domain were included in the degradon.

Protein Purification.

Yeast proteasome was purified from *S. cerevisiae* strain YYS40 (MATa rpn11::RPN11 3×FLAG-HIS3 leu2 his3 trp1 ade2 can1 ssd1) by immunoaffinity chromatography using FLAG antibodies (M2 agarose affinity beads, Sigma) as previously described[56]. Proteasome preparations were analyzed by SDS-PAGE and compared to published compositions. Each proteasome preparation was checked for activity by testing degradation of the positive control proteasome substrate UbL-GFP-tail.

The substrates and degradons used for the in vitro degradation assays were overexpressed in and purified from *E.*

*coli* using standard methodologies. Bacterial strains were grown in 1 L of 2XYT media at 37° C. to an optical density of 0.6-1.0. Protein expression was induced with 0.25-1 mM isopropyl β-D-1-thiogalactopyranoside (IPTG), and incubation continued overnight at 16° C. Cells were harvested by centrifugation, resuspended in ice-cold NPI-10 buffer (50 mM sodium phosphate pH 7.4, 300 mM NaCl, and 10 mM imidazole) and homogenized using the Avestin Emulsiflex C3 (2-3 passes) at 15,000 psi. The cell lysate was incubated with Ni-NTA metal affinity beads (GE Healthcare) and nutated for 30 min at 4° C. This mixture was applied to a gravity column, and washed with five column volumes of NPI-10 buffer, then five column volumes NPI-20 buffer (NPI-10 with 20 mM imidazole). The protein was eluted from the resin with NPI-250 buffer (NPI-10 with 250 mM imidazole). The elution was desalted by PD-10 desalting column (GE Healthcare) and into Chitin-column binding buffer (CBB) (20 mM Tris pH 7.4, 300 mM NaCl, and 0.5 mM EDTA). This was bound to Chitin beads (NEB) then washed with 50 column volumes of CBB. The protein was eluted after an overnight incubation with Chitin cleavage buffer (CBB with 100 mM dithiothreitol) and buffer exchanged into storage buffer (20 mM Tris pH 7.4, 150 mM NaCl, 10% glycerol). Protein concentration was measured using absorbance at 280 and the extinction coefficient from the proteins' sequence (ExPASy's ProtParam). The identity and purity of purified proteins was confirmed by SDS-PAGE.

Substrate Degradation Assay.

The degradation of fluorescent substrate (SH2-GFP-tail) in vitro was monitored by fluorescence intensity and performed in 384-well plate on a Tecan plate reader (Infinite® M1000 PRO, Tecan). Assays were carried out at 30° C. by adding fluorescent substrates to 25-40 nM of purified yeast proteasome in a reaction buffer containing a creatine-phosphate/creatine kinase/ATP regenerating system[54]. Fluorescence intensity was read every minute at the excitation wavelength of 388 nm and the emission wavelength of 420 nm for 75 minutes. Protein amount was calculated based on fluorescence intensity of the reaction in each well and the standard curves describing the correlation between fluorescence intensity and protein concentration.

Each assay was repeated at least two times. Initial degradation rates are given by the slope of the decay curves at time zero and are calculated as the product of the amplitude and the rate constant of the decay curve determined by nonlinear fitting to a single exponential decay in the software package Kaleidagraph (version 4.1, Synergy Software).

Mammalian Construct Design.

The substrate of Abl or Shp2 SH2-GFP-tail was cloned into pcDNA5/FRT/TO using the In Fusion® cloning kit (Clontech). The binding degradon, consisting of human Rad23b UbL domain fused N-terminally to the monobody (HA4, Nsa1, or Cs1), was cloned using restriction enzymes into a pcDNA3 vector containing an N-terminal FLAG tag and C-terminal Internal Ribosome Entry Site (IRES) followed by mCherry. The resulting constructs were FLAG-hUbL-mB-IRES-mCherry. The non-binding degradon was created by changing HA4 Tyr87 to Ala using the QuikChange Site-Directed Mutagenesis kit (Agilent) to generate FLAG-hUbL-mB$^{HA4(Y87A)}$-IRES-mCherry.

Stable Cell Generation.

Stable HEK293 Flp-In™ cells expressing the substrate (Shp2 or Abl SH2-GFP-tail) were generated using the Flp-In™ system (Life Technologies) according to manufacturer's instructions. Briefly, Flp-In™-293 host cells were transfected with 1 μg substrate DNA in pcDNA5/FRT/TO plasmid and 9 μg pOG44 plasmid encoding Flp recombinase in OPTI-MEM (Life Technologies) with Lipofectamine® 2000 in a 6-well plate. 24 hours later, OPTI-MEM was replaced with Dulbecco's Modified Eagle's Medium (Gibco) supplemented with 10% fetal bovine serum (FBS) and 1% penicillin/streptomycin (pen/strep) and cells were allowed to recover overnight. Cells were trypsinized the next day and plated on 10 cm$^2$ plates in fresh medium. Medium was replaced 24 hours later with DMEM supplemented with 10% FBS, 1% pen/strep, and 200 μg/mL hygromycin B (Gibco). Medium was replaced every two to three days with fresh selective medium until colonies formed. All colonies were considered to be isogenic and the whole plate was trypsinized and plated into fresh selective medium in a 75 cm$^2$ dish, then subcultured according to manufacturer's instructions. Aliquots of cells were frozen in FBS supplemented with 10% DMSO by cooling at −1° C./min at −80° C. and stored in a −150° C. freezer until further use.

Transfections and Assays.

HEK293 Flp-In™ host and SH2-GFP-tail stable cells were transfected with either binding (FLAG-hUbL-mB-IRES-mCherry) or non-binding degradon (FLAG-hUbL-mB$^{HA4(Y87A)}$-IRES-mCherry) or water (vehicle) with Lipofectamine® 2000 reagent according to manufacturer's instructions in 6-well plates. For immunoblot analysis, 48 hours after transfection, cells were harvested and lysed in whole-cell extract buffer (50 mM Tris pH8.0, 280 mM NaCl, 10% glycerol, 0.5% NP-40, 0.2 mM EDTA, 2 mM EGTA, 1 mM dithiothreitol, 1 mM orthovanadate, and protease inhibitor cocktail from Roche) and cleared by centrifugation. ~50-100 μg of cellular lysate was used for Western blotting. Antibodies used were: primary rabbit anti-Actin (Sigma), mouse anti-Shp2 (Santa Cruz, clone B-1), mouse anti-FLAG (Sigma), secondary IR dye 800 goat anti-mouse (Rockland), and Alexa Fluor 680 goat anti-rabbit (Invitrogen).

For Fluorescence Activated Cell Sorting (FACS), 48 hours after transfection, cells were trypsinized and neutralized in DMEM without phenol red supplemented with 10% FBS and 1% pen/strep. FACS data were collected on a BD Fortessa flow cytometer. Data were analyzed using FlowJo software (version 3.0).

For endogenous protein immunostaining, 72 hours post transfection, cells were trypsinized and neutralized in DMEM without phenol red (Gibco) supplemented with 10% FBS. Cells were washed once with D-PBS (Gibco), then fixed with 0.25% formaldehyde (from Formalin containing 4% formaldehyde, Sigma) for 20 minutes on ice. Cells were washed with PBS then permeabilized with 90% methanol in PBS for 30 minutes on ice. After washing with PBS, cells were blocked for one hour with PBS plus 0.5% BSA. Cells were washed and primary mouse anti-Shp2 antibody (Santa Cruz, clone B-1) was added at a 1:500 concentration and incubated overnight at 4° C. Cells were washed twice and then secondary goat anti-mouse IgG conjugated to Alexa Fluor 488 (Invitrogen) was added at a 1:2500 concentration. Cells were washed and then analyzed via FACS as above.

SDS-PAGE fluorescence analysis was carried out on unboiled samples with a Typhoon FLA 7000 (GE Healthcare) with filters set at 488 nm (GFP) and 555 nm (mCherry). Images were quantified using ImageJ software.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

1. Seyhan, A. A. RNAi: a potential new class of therapeutic for human genetic disease. *Hum. Genet.* 130, 583-605 (2011).
2. Grimm, D. et al. Fatality in mice due to oversaturation of cellular microRNA/short hairpin RNA pathways. *Nature* 441, 537-541 (2006).
3. Kim, D. H. & Rossi, J. J. Strategies for silencing human disease using RNA interference. *Nature Reviews Genetics* 8, 173-184 (2007).
4. Sakamoto, K. M. et al. Protacs: chimeric molecules that target proteins to the Skp1-Cullin-F box complex for ubiquitination and degradation. *Proc Natl Acad Sci USA* 98, 8554-8559 (2001).
5. Sakamoto, K. M. Protacs for treatment of cancer. *Pediatr. Res.* 67, 505-508 (2010).
6. Komander, D. & Rape, M. The ubiquitin code. *Annu Rev Biochem* 81, 203-229 (2012).
7. Deshaies, R. J. & Joazeiro, C. A. P. RING domain E3 ubiquitin ligases. *Annu Rev Biochem* 78, 399-434 (2009).
8. Schrader, E. K., Wilmington, S. R., Matouschek, A. & Matouschek, A. Making it easier to regulate protein stability. *Chem Biol* 17, 917-918 (2010).
9. Tomko, R. J. & Hochstrasser, M. Molecular architecture and assembly of the eukaryotic proteasome. *Annu Rev Biochem* 82, 415-445 (2013).
10. Bhattacharyya, S., Yu, H., Mim, C., Matouschek, A. & Matouschek, A. Regulated protein turnover: snapshots of the proteasome in action. *Nat Rev Mol Cell Biol* 15, 122-133 (2014).
11. Dohmen, R. J., Willers, I. & Marques, A. J. Biting the hand that feeds: Rpn4-dependent feedback regulation of proteasome function. *Biochim Biophys Acta* 1773, 1599-1604 (2007).
12. Xie, Y. & Varshavsky, A. RPN4 is a ligand, substrate, and transcriptional regulator of the 26S proteasome: a negative feedback circuit. *Proc Natl Acad Sci USA* 98, 3056-3061 (2001).
13. Kwak, M.-K., Wakabayashi, N., Greenlaw, J. L., Yamamoto, M. & Kensler, T. W. Antioxidants enhance mammalian proteasome expression through the Keap1-Nrf2 signaling pathway. *Mol Cell Biol* 23, 8786-8794 (2003).
14. Radhakrishnan, S. K. et al. Transcription factor Nrf1 mediates the proteasome recovery pathway after proteasome inhibition in mammalian cells. *Mol Cell* 38, 17-28 (2010).
15. Meiners, S. et al. Inhibition of proteasome activity induces concerted expression of proteasome genes and de novo formation of Mammalian proteasomes. *J Biol Chem* 278, 21517-21525 (2003).
16. Oerlemans, R. et al. Molecular basis of bortezomib resistance: proteasome subunit beta5 (PSMB5) gene mutation and overexpression of PSMB5 protein. *Blood* 112, 2489-2499 (2008).
17. Ravid, T. & Hochstrasser, M. Diversity of degradation signals in the ubiquitin-proteasome system. *Nat Rev Mol Cell Biol* 9, 679-690 (2008).
18. Schrader, E. K., Harstad, K. G., Matouschek, A. & Matouschek, A. Targeting proteins for degradation. *Nat Chem Biol* 5, 815-822 (2009).
19. Perkel, J. M. RNAi Therapeutics: A two-year update. *Science* 324, 454-456 (2009).
20. Hicke, L., Schubert, H. L. & Hill, C. P. Ubiquitin-binding domains. *Nat Rev Mol Cell Biol* 6, 610-621 (2005).
21. Janse, D. M., Crosas, B., Finley, D. & Church, G. M. Localization to the proteasome is sufficient for degradation. *J Biol Chem* 279, 21415-21420 (2004).
22. Zhang, M., MacDonald, A. I., Hoyt, M. A. & Coffino, P. Proteasomes begin ornithine decarboxylase digestion at the C terminus. *J Biol Chem* 279, 20959-20965 (2004).
23. Zhang, M., Pickart, C. M. & Coffino, P. Determinants of proteasome recognition of ornithine decarboxylase, a ubiquitin-independent substrate. *EMBO J* 22, 1488-1496 (2003).
24. Kraut, D. A. et al. Sequence- and species-dependence of proteasomal processivity. *ACS Chem Biol* 7, 1444-1453 (2012).
25. Koodathingal, P. et al. ATP-dependent proteases differ substantially in their ability to unfold globular proteins. *J Biol Chem* 284, 18674-18684 (2009).
26. Lee, C., Schwartz, M. P., Prakash, S., Iwakura, M. & Matouschek, A. ATP-dependent proteases degrade their substrates by processively unraveling them from the degradation signal. *Mol Cell* 7, 627-637 (2001).
27. Finley, D. Recognition and processing of ubiquitin-protein conjugates by the proteasome. *Annu Rev Biochem* 78, 477-513 (2009).
28. Elsasser, S. & Finley, D. Delivery of ubiquitinated substrates to protein-unfolding machines. *Nat Cell Biol* 7, 742-749 (2005).
29. Elsasser, S., Chandler-Militello, D., Müller, B., Hanna, J. & Finley, D. Rad23 and Rpn10 serve as alternative ubiquitin receptors for the proteasome. *J Biol Chem* 279, 26817-26822 (2004).
30. Hiyama, H. et al. Interaction of hHR23 with S5a. The ubiquitin-like domain of hHR23 mediates interaction with S5a subunit of 26 S proteasome. *J Biol Chem* 274, 28019-28025 (1999).
31. Schauber, C. et al. Rad23 links DNA repair to the ubiquitin/proteasome pathway. *Nature* 391, 715-718 (1998).
32. Heinen, C., Acs, K., Hoogstraten, D. & Dantuma, N. P. C-terminal UBA domains protect ubiquitin receptors by preventing initiation of protein degradation. *Nat Commun* 2, 191 (2011).
33. Fishbain, S. et al. Rad23 escapes degradation because it lacks a proteasome initiation region. *Nat Commun* 2, 192 (2011).
34. Koide, A., Bailey, C. W., Huang, X. & Koide, S. The fibronectin type III domain as a scaffold for novel binding proteins. *J Mol Biol* 284, 1141-1151 (1998).

35. Lipovsek, D. Adnectins: engineered target-binding protein therapeutics. *Protein Engineering Design and Selection* 24, 3-9 (2011).
36. Fellouse, F. A. et al. High-throughput generation of synthetic antibodies from highly functional minimalist phage-displayed libraries. *J Mol Biol* 373, 924-940 (2007).
37. Koide, A., Wojcik, J., Gilbreth, R. N., Hoey, R. J. & Koide, S. Teaching an old scaffold new tricks: monobodies constructed using alternative surfaces of the FN3 scaffold. *J Mol Biol* 415, 393-405 (2012).
38. Wojcik, J. et al. A potent and highly specific FN3 monobody inhibitor of the Abl SH2 domain. *Nat Struct Mol Biol* 17, 519-527 (2010).
39. Grebien, F. et al. Targeting the SH2-kinase interface in Bcr-Abl inhibits leukemogenesis. *Cell* 147, 306-319 (2011).
40. Sha, F. et al. Dissection of the BCR-ABL signaling network using highly specific monobody inhibitors to the SHP2 SH2 domains. *Proceedings of the National Academy of Sciences* 110, 14924-14929 (2013).
41. Li, G. N., Wang, S. P., Xue, X., Qu, X. J. & Liu, H. P. Monoclonal antibody-related drugs for cancer therapy. *Drug Discov Ther* 7, 178-184 (2013).
42. Bloom, L. & Calabro, V. FN3: a new protein scaffold reaches the clinic. *Drug Discov. Today* 14, 949-955 (2009).
43. Druker, B. J. et al. Effects of a selective inhibitor of the Abl tyrosine kinase on the growth of Bcr-Abl positive cells. *Nat Med* 2, 561-566 (1996).
44. Druker, B. J. Translation of the Philadelphia chromosome into therapy for CML. *Blood* 112, 4808-4817 (2008).
45. Jabbour, E., Hochhaus, A., Cortes, J., La Rosée, P. & Kantarjian, H. M. Choosing the best treatment strategy for chronic myeloid leukemia patients resistant to imatinib: weighing the efficacy and safety of individual drugs with BCR-ABL mutations and patient history. *Leukemia* 24, 6-12 (2010).
46. Hamilton, A. et al. Chronic myeloid leukemia stem cells are not dependent on Bcr-Abl kinase activity for their survival. *Blood* 119, 1501-1510 (2012).
47. Tsien, R. Y. The green fluorescent protein. *Annu Rev Biochem* 67, 509-544 (1998).
48. Remington, S. J. Green fluorescent protein: a perspective. *Protein Sci* 20, 1509-1519 (2011).
49. Corish, P., Corish, P., Tyler-Smith, C. & Tyler-Smith, C. Attenuation of green fluorescent protein half-life in mammalian cells. *Protein Eng.* 12, 1035-1040 (1999).
50. Nager, A. R., Baker, T. A. & Sauer, R. T. Stepwise unfolding of a β barrel protein by the AAA+ClpXP protease. *J Mol Biol* 413, 4-16 (2011).
51. Prakash, S., Tian, L., Ratliff, K. S., Lehotzky, R. E. & Matouschek, A. An unstructured initiation site is required for efficient proteasome-mediated degradation. *Nat Struct Mol Biol* 11, 830-837 (2004).
52. Prakash, S., Inobe, T., Hatch, A. J. & Matouschek, A. Substrate selection by the proteasome during degradation of protein complexes. *Nat Chem Biol* 5, 29-36 (2009).
53. Heessen, S., Masucci, M. G. & Dantuma, N. P. The UBA2 domain functions as an intrinsic stabilization signal that protects Rad23 from proteasomal degradation. *Mol Cell* 18, 225-235 (2005).
54. Fishbain, S. et al. Sequence composition of disordered regions fine-tunes protein half-life. *Nat Struct Mol Biol* 22, 214-221 (2015).
55. Sleight, S. C. & Sauro, H. M. BioBrick™ assembly using the In-Fusion PCR Cloning Kit. *Methods Mol. Biol.* 1073, 19-30 (2013).
56. Saeki, Y., Isono, E. & Toh-E, A. Preparation of ubiquitinated substrates by the PY motif-insertion method for monitoring 26S proteasome activity. *Meth Enzymol* 399, 215-227 (2005).
57. Lee, J. O., Russo, A. A. & Pavletich, N. P. Structure of the retinoblastoma tumour-suppressor pocket domain bound to a peptide from HPV E7. *Nature* 391, 859-865 (1998).
58. Berezutskaya, E. & Bagchi, S. The human papillomavirus E7 oncoprotein functionally interacts with the S4 subunit of the 26 S proteasome. *J Biol Chem* 272, 30135-30140 (1997).
59. Whitby, F. G. & Hill, C. P. A versatile platform for inactivation and destruction. *Structure* 15, 137-138 (2007).
60. Higashitsuji, H. et al. Reduced stability of retinoblastoma protein by gankyrin, an oncogenic ankyrin-repeat protein overexpressed in hepatomas. *Nat Med* 6, 96-99 (2000).
61. Dawson, S. et al. Gankyrin is an ankyrin-repeat oncoprotein that interacts with CDK4 kinase and the S6 ATPase of the 26 S proteasome. *J Biol Chem* 277, 10893-10902 (2002).
62. Nakamura, Y. et al. Structure of the oncoprotein gankyrin in complex with S6 ATPase of the 26S proteasome. *Structure* 15, 179-189 (2007).
63. Liu, H. et al. In vitro and in vivo modifications of recombinant and human IgG antibodies. *MAbs* 6, 1145-1154 (2014).
64. Holliger, P. & Hudson, P. J. Engineered antibody fragments and the rise of single domains. *Nat Biotechnol* 23, 1126-1136 (2005).
65. Soucek, L. et al. Modelling Myc inhibition as a cancer therapy. *Nature* 455, 679-683 (2008).
66. Kortemme, T. & Baker, D. Computational design of protein-protein interactions. *Current opinion in chemical biology* 8, 91-97 (2004).
67. Sood, V. D. & Baker, D. Recapitulation and design of protein binding peptide structures and sequences. *J Mol Biol* 357, 917-927 (2006).
68. Wadia, J. S., Stan, R. V. & Dowdy, S. F. Transducible TAT-HA fusogenic peptide enhances escape of TAT-fusion proteins after lipid raft macropinocytosis. *Nat Med* 10, 310-315 (2004).
69. Erazo-Oliveras, A. et al. Protein delivery into live cells by incubation with an endosomolytic agent. *Nature Methods* 11, 861-867 (2014).
70. Stewart, K. M., Horton, K. L. & Kelley, S. O. Cell-penetrating peptides as delivery vehicles for biology and medicine. *Org. Biomol. Chem.* 6, 2242-2255 (2008).
71. Mohanty, C., Das, M., Kanwar, J. R. & Sahoo, S. K. Receptor mediated tumor targeting: an emerging approach for cancer therapy. *Curr Drug Deliv* 8, 45-58 (2011).
72. Jain, R. A. The manufacturing techniques of various drug loaded biodegradable poly(lactide-co-glycolide) (PLGA) devices. *Biomaterials* 21, 2475-2490 (2000).
73. Su, X., Fricke, J., Kavanagh, D. G. & Irvine, D. J. In vitro and in vivo mRNA delivery using lipid-enveloped pH-responsive polymer nanoparticles. *Mol. Pharm.* 8, 774-787 (2011).

74. Ylä-Herttuala, S. Endgame: glybera finally recommended for approval as the first gene therapy drug in the European union. *Mol. Ther.* 20, 1831-1832 (2012).

75. Gardner, M. R. et al. AAV-expressed eCD4-Ig provides durable protection from multiple SHIV challenges. *Nature* 519, 87-91 (2015).

What is claimed is:

1. A recombinant polypeptide that binds to a target polypeptide, the recombinant polypeptide comprising a target-binding domain and a proteasome-binding domain that comprises a ubiquitin-like domain, wherein said target binding domain comprises an antibody or a fragment thereof that binds to the target polypeptide.

2. The polypeptide of claim 1, wherein the target polypeptide is a polypeptide associated with a disease.

3. The polypeptide of claim 1, wherein the target polypeptide is not a reporter protein; wherein the target-binding domain does not bind to the Huntingtin protein (HTT); or wherein the target-binding domain does not bind to protein having a poly-Q sequence.

4. The polypeptide of claim 1, wherein the target-binding domain is position N-terminally relative to the proteasome binding domain.

5. The polypeptide of claim 1, wherein the target-binding domain is position C-terminally relative to the proteasome binding domain.

6. The polypeptide of claim 1, wherein the proteasome-binding domain comprises a domain from human Rad23b.

7. The polypeptide of claim 6, wherein the proteasome-binding domain comprises amino acids 1-83 of human Rad23b.

8. The polypeptide of claim 1, wherein the target-binding domain and the proteasome-binding domain are separated by a linker.

9. The polypeptide of claim 1, further comprising a cell-penetrating peptide (CPP) sequence or a cellular receptor-binding sequence.

10. The polypeptide of claim 1, wherein the antibody or antibody fragment comprises a monobody or scFv.

11. The polypeptide of claim 10, wherein the antibody or antibody fragment comprises the HA4 monobody, Nsa1 monobody, and/or the Cs1 monobody.

12. The polypeptide of claim 1, wherein the target-binding domain binds to a prion, a viral polypeptide, a disease-associated protein, a cellular polypeptide having a disease-associated mutation or the product of an oncogene.

13. The polypeptide of claim 12, wherein the target-binding domain binds to the product of an oncogene.

14. The polypeptide of claim 12, wherein the oncogene is Abl and/or Shp2.

15. The polypeptide of claim 12, wherein the target binding domain binds to the SH2 domain of Abl, the N-terminal SH2 domain of Shp2, and/or C-terminal SH2 domain of Shp2.

16. The polypeptide of claim 12, wherein the target-binding domain binds to misfolded beta-amyloid.

17. A nucleic acid molecule encoding a polypeptide according to claim 1.

18. A pharmaceutical composition comprising: a polypeptide according to claim 1.

19. The polypeptide of claim 1, wherein the target binding domain comprises a monobody that binds to the target polypeptide.

20. The polypeptide of claim 1, wherein the target binding domain comprises an scFv that binds to the target polypeptide.

21. The polypeptide of claim 1, wherein the target binding domain comprises an antibody that binds to the target polypeptide.

* * * * *